United States Patent
Watanabe et al.

(10) Patent No.: US 7,871,644 B2
(45) Date of Patent: *Jan. 18, 2011

(54) PHARMACEUTICAL COMPOSITION FOR ORAL USE WITH IMPROVED ABSORPTION

(75) Inventors: Shunsuke Watanabe, Shizuoka (JP); Shigeo Takemura, Shizuoka (JP); Yuuki Tsutsui, Shizuoka (JP); Himoru Kondo, Shizuoka (JP); Kiyo Nakanishi, Shizuoka (JP); Kazuhiro Sako, Shizuoka (JP); Toyohiro Sawada, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 339 days.

This patent is subject to a terminal disclaimer.

(21) Appl. No.: 10/949,114

(22) Filed: Sep. 10, 2004

(65) Prior Publication Data

US 2005/0112206 A1    May 26, 2005

Related U.S. Application Data

(63) Continuation of application No. 09/907,557, filed on Jul. 16, 2001, now Pat. No. 7,008,640.

(60) Provisional application No. 60/218,980, filed on Jul. 17, 2000.

(51) Int. Cl.
*A61K 9/22* (2006.01)
*A61K 9/20* (2006.01)
*A61K 9/28* (2006.01)
*A61K 9/32* (2006.01)
*A61K 9/48* (2006.01)

(52) U.S. Cl. .................... 424/468; 424/451; 424/452; 424/464; 424/465; 424/474; 424/489

(58) Field of Classification Search ............... 424/451, 424/458
See application file for complete search history.

(56) References Cited

U.S. PATENT DOCUMENTS 4,786,508 A    11/1988    Ghebre-Sellassi (Continued)

FOREIGN PATENT DOCUMENTS

EP    0413299 A1    2/1991

(Continued)

OTHER PUBLICATIONS

Kirk-Othmer; Encyclopedia of Chemical Technology; 4th Ed.; 1997; pp. 571-590; vol. 22; Wiley-Interscience Publication.

(Continued)

*Primary Examiner*—Humera N Sheikh
(74) *Attorney, Agent, or Firm*—Townsend and Townsend and Crew LLP

(57) ABSTRACT

The present invention presents a pharmaceutical composition for oral use with improved absorption, which comprises drug, aminoalkyl methacrylate copolymer E, and acidic substance and is obtained by bringing said 3 components together and uniformly mixing at least this polymer and this acidic substance, and a method of improving oral absorption/by using this pharmaceutical composition. Moreover, the present invention presents an agent for improving oral absorption that increases drug permeability of the digestive tract mucous membrane and/or mucous layer present on the surface of this membrane, whose active ingredient is aminoalkyl methacrylate copolymer E. In addition, the present invention presents an oral agent for improving absorption by increasing drug permeability of the digestive tract mucous membrane and/or the mucous layer distributed over this mucous membrane, whose effective component is aminoalkyl methacrylate copolymer E.

17 Claims, 4 Drawing Sheets

U.S. PATENT DOCUMENTS

| | | | |
|---|---|---|---|
| 5,102,668 | A | 4/1992 | Eichel et al. |
| 5,431,920 | A * | 7/1995 | Bechard |
| 5,445,830 | A * | 8/1995 | Ishizue et al. ............... 424/484 |
| 5,456,923 | A | 10/1995 | Nakamichi et al. |
| 6,143,326 | A | 11/2000 | Mockel et al. |
| 6,153,220 | A | 11/2000 | Cumming et al. |
| 6,245,353 | B1 | 6/2001 | Tritthart et al. |
| 6,359,011 | B1 * | 3/2002 | Bess et al. ................. 514/646 |
| 2005/0037084 | A1 | 2/2005 | Nomura et al. |

FOREIGN PATENT DOCUMENTS

| | | | |
|---|---|---|---|
| EP | 1 093 818 | A1 | 4/2001 |
| EP | 1093818 | A1 * | 4/2001 |
| EP | 1273306 | A1 | 8/2003 |
| JP | 2015027 | | 1/1990 |
| JP | 2-268178 | A | 11/1990 |
| JP | 3-74396 | A | 3/1991 |
| JP | 4-208225 | A | 7/1992 |
| JP | 4-327529 | | 11/1992 |
| JP | 5-255075 | A | 10/1993 |
| JP | 6-116138 | A | 4/1994 |
| JP | 10-504020 | A | 4/1998 |
| WO | WO 96/34628 | A1 | 11/1996 |
| WO | WO00/02574 | | 1/2000 |
| WO | WO 00/15261 | A1 | 3/2000 |
| WO | WO 00/43041 | A1 | 7/2000 |

OTHER PUBLICATIONS

Degussa; Röhm Pharma Polymers; viewed on Aug. 19, 2009 at: http://www.rohacell.com/en/pharmapolymers/service/literature/practical_course.Par.0001.TRow.003.TCell.003.File.tmp/pc_10_enteric.pdf.

H. M. El-Sabbagh, et al., "Effect of Some Additives on the Properties of Phenazopyridine Hydrochloride Granules and Their Corresponding Tablets", *Pharmazie*, vol. 39, No. 6, pp. 404-406, (1984).

J. Karlsson, et al., "The mucus layer as a barrier to drug absorption in monolayers of human intestinal epithelial HT29-H goblet cells", *Int. J. Pharm.*, 99, pp. 209-218, (1993).

I. W. Kellaway, et al., "The influence of mucin on the bioavailability of tetracycline", *J. Pharm. Pharmac.*, 27 (4), pp. 281-283, (1975).

A. W. Larhed, et al., "Diffusion of Drugs in Native and Purified Gastrointestinal Mucus", *J. Pharm. Sci.*, vol. 86, No. 6, pp. 660-665, (1997).

S. J. Houston, et al., "The Absorption of the Oral Bisphosphonate Pamidronate under Different Dietary Conditions", *Br. J. Cancer*, 71, Suppl. 24, 67, (1995).

H. Lennernås, et al., "Evidence for an Interaction Between the β-Blocker Pafenolol and Bile Salts in the Intestinal Lumen of the Rat Leading to Dose-Dependent Oral Absorption and Double Peaks in the Plasma Concentration-Time Profile", *Pharm. Res.*, vol. 10, No. 6, pp. 879-883, (1993).

K. Morimoto, et al., "Effect of Hyaluronidase on the Small Intestinal Absorption of Drugs in Rats", *J. Pharmacobio-Dyn.*, 9, No. 6, s-58, (1986).

A. Wikman, et al., "A Drug Absorption Model Based on the Mucus Layer Producing Human Intestinal Goblet Cell Line HT29-H", *Pharm. Res.*, vol. 10, No. 6, pp. 843-852, (1993).

H. Asada, et al., "Absorption Characteristics of Chemically Mdified-Insulin Derivatives with Various Fatty Acids in the Small and Large Intestine", *J. Pharm. Sci.*, vol. 84, No. 6, pp. 682-687, (1995).

L. Hovgaard, et al., "Insulin stabilization and GI absorption", *J. Controlled Release*, vol. 19, No. 1-3, pp. 99-108, (1992).

J. H. Lin, et al., "Factors Affecting Oral Absorption of Alendronate, a Potent Antiosteolytic Bisphosphonate, in Rats", *Pharm. Res.*, vol. 8, No. 10, Suppl., S273, (1991).

N. G.M. Schipper, et al., "Chitosans as absorption enhancers of poorly absorbable drugs 3: Influence of mucus on absorption enhancement", *Eur. J. Pharm. Sci.*, 8, No. 4, pp. 335-343, (1999).

M. P. Braybrooks, et al., "The effect of mucin on the bioavailability of tetracycline from the gastrointestinal tract; in vivo, in vitro correlations", *J. Pharm. Pharmac.*, 27, pp. 508-515, (1975).

A. W. Larhed, et al., "The Influence of Intestinal Mucus Components on the Diffusion of Drugs", *Pharm. Res.*, vol. 15, No. 1, pp. 66-71, (1998).

T. Usui, et al., "Sensitive determination of a novel bisphosphonate, YM529, in plasma, urine and bone by high-performance liquid chromatography with fluorescence detection", *J. Chromatogr. B*, 652, pp. 67-72, (1994).

Röhm Pharma, "EUDRAGIT®E Application in the Production of Pharmaceutical Preparations", Prospectus (Info E-1/e), pp. 2-7, 2005.

Polymeric Materials Science and Engineering; vol. 11, No. 1, Jan. 1995.

* cited by examiner (1-1)

(1-2a)

(1-2b)

PHARMACEUTICAL COMPOSITION FOR ORAL USE WITH IMPROVED ABSORPTION

CROSS-REFERENCES TO RELATED APPLICATIONS

This application claims priority to U.S. Provisional Application No. 60/218,980, filed Jul. 17, 2000, and to U.S. Application Ser. No. 09/907,557, filed Jul. 16, 2001, the disclosures of which are hereby incorporated by reference in their entirety for all purposes.

TECHNICAL FIELD OF THE INVENTION

The present invention pertains to an oral agent for improving absorption that enhances drug permeability of the digestive tract mucous membrane and/or mucous layer distributed over this mucous membrane, whose effective component is aminoalkyl methacrylate copolymer E, and to use as an oral agent for improving absorption that enhances drug permeability of the digestive tract mucous membrane and/or mucous layer distributed over this mucous membrane, whose effective component is aminoalkyl methacrylate copolymer E. Moreover, the present invention pertains to a pharmaceutical composition for oral use with improved absorption comprising aminoalkyl methacrylate copolymer E, which is particularly suitable for this enhancement of drug permeability of the digestive tract mucous membrane and/or mucous layer and improvement of oral absorptivity.

BACKGROUND OF THE INVENTION

Drugs that have been administered orally quickly pass through the esophagus to reach the stomach. The stomach walls are made from the 3 layers of mucous membrane, muscle layer, and serous membrane. However, in contrast to the small intestine, the effective surface area for absorption is small, and therefore, with the exception of some drugs, the stomach plays a small role as an absorption site. On the other hand, the small intestine of humans consists of the duodenum, jejunum, and ileum. It is the longest of the digestive tract and its effective surface area for absorption is large. Therefore, it is the ideal site for absorption of many drugs. However, epithelial cells, which have a plasma membrane made from a lipid double layer, cover the surface of the digestive tract mucous membrane site very closely and therefore, absorption is strongly restricted in the case of drugs that are very water soluble and polymer drugs. Moreover, in addition to the digestive tract mucous membrane, the mucous layer that ordinarily covers the digestive tract mucous membrane also becomes a barrier blocking the absorption of drugs by the digestive tract. Consequently, drugs that have been orally administered are first absorbed in vivo after passing through the above-mentioned two barriers of the mucous layer covering the mucous membrane surface and the mucous membrane.

The above-mentioned mucous layer is mainly made from the components of, glycoprotein such as mucin, cholesterol, lipids such as linoleic acid, proteins, DNA, and others, including various metal ions, such as calcium ions, etc. Moreover, the mucous membrane also contains traces of metal ions, etc. Consequently, drugs that are difficult to absorb through the digestive tract because of interaction with various biologically-derived components are present in the mucous layer and/or mucous membrane of the digestive tract.

For instance, bisphosphonate compounds have (P—C—P) bonds in their molecular structure and therefore, as with phosphonate compounds in general, have strong affinity with bivalent metal ions, such as calcium ions, etc., and bond with these metal ions to form insoluble complexes. Consequently, when bisphosphonate compounds are taken after eating or simultaneously with calcium agent, a slightly soluble complex is formed in the digestive tract and therefore, absorptivity of the bisphosphonate compound in the digestive tract is markedly reduced.

Moreover, it is known that there are cases where digestive tract absorption is blocked with substances that form complexes of inferior permeability of the mucous layer and mucous membrane, such as complexes of drugs and bile acids, etc.

Furthermore, the absorption route, solubility, lipophilicity, molecular weight, decomposition by digestive enzymes etc., of the drug are considered to be other factors that block digestive tract absorption.

The drug absorption routes include the route of passage through the cell membrane of mucous membrane cells and the route of passage through spaces between cells. In order for a drug to be absorbed, the drug must dissolve by either route. Consequently, drugs are slightly soluble and drugs that form an insoluble complex with in vivo components are difficult to absorb. In the case of the route of passage through the cell membrane, the drug must pass through the lipid membrane of the cell and therefore, drugs of low lipophilicity are generally difficult to absorb.

As explained above, there appear to be various reasons why drugs are difficult to absorb through the mucous layer and/or mucous membrane of the digestive tract.

The fact that drugs have difficulty passing through the mucous layer of the digestive tract has been reported many times in the past. For instance, J. Karlsson et al. report that the mucous layer accounts for 78% of the barrier to absorption of testosterone (Int. J. Pharm., 1993). Moreover, I. W. Kellaway et al. report that the mucous layer reduces bioavailability of tetracycline by 50% (J. Pharm. Pharmacol., 27 (4), pp. 281-283, 1975). Furthermore, A. W. Larhed et al. also report that the mucous layer reduces the diffusion coefficient of testosterone by 50% (J. Pharm. Sci, 86, pp. 660-665, 1997). In addition, it is reported that bisphosphonate compounds form a chelate with calcium ions within the digestive tract to produce an insoluble complex and absorption from the digestive tract is thereby reduced (Br. J. Cancer, 71, Suppl. 24, 67, 1995). It is also reported that the absorption of pafenolol from the small intestine was inhibited by interaction with bile acids (Pharmaceutical Research, 10(6): pp. 879-83, 1993).

Consequently, enhancement of in vivo absorption of a drug by preventing interaction with the mucous layer or a substance present in the mucous layer or mucous membrane and/or enhancement of digestive tract absorption of a drug by improving drug permeability through cells and/or spaces between cells when the digestive tract mucous membrane is affected, targeted at drugs that are difficult to absorb from the digestive tract due to interaction with the digestive tract mucous layer and/or mucous membrane, including drugs that are difficult to absorb from the digestive tract because permeability of the mucous layer present on the digestive tract mucous membrane is poor, drugs that form an insoluble complex by interaction with a substance present in the mucous layer and are therefore difficult to absorb, drugs that are difficult to absorb from the digestive tract because of poor permeability of the mucous membrane of the digestive tract, etc., is an important technical topic in terms of hoping for satisfactory pharmacological activity from a drug.

On the other hand, the following methods are known as technology for improving permeability of drugs through the digestive tract mucous layer:

For instance, K. Morimoto et al., report increasing absorption of sulfaguanidine, phenol red or scopolamine by the addition hyaluronidase (J. Pharmacobiodyn, 9, No. 6, s-58, 1986), A Wikman et al. report reducing the mucous layer and improving permeability of testosterone by the addition of N-acetylcysteine (Pharm. Res., 10, No. 6, pp 843-852, (1993)), H. Asada et al. report improving permeability of the mucous layer of the duodenum and large intestine by modification of insulin with caproic acid (J. Pharm. Sci., 84, No. 6, pp. 682-687, 1995), and L. Hovgaard et al. report improving dispersion in the mucous layer by forming a compound of dodecyl maltoside and insulin (J. Controlled Release, 19, No. 1-3, pp. 99-108, 1992). Nevertheless, these methods are technologies for improving drug migration through the mucous layer by reducing the mucous layer or forming a specific drug complex and are not means for improving oral absorption by preventing interaction between a drug and components of the mucous layer and mucous membrane.

Furthermore, J. H. Lin et al. report that absorption of alendronate (4-amino-1-hydroxy butylidene 1,1-bisphosphonate), whose absorption is reduced due to the formation of a compound with calcium ions in vivo, is increased by chelators, such as EDTA, citric acid, etc. (Pharm. Res., 8, No. 10, Suppl., S273, 1991), but this method is simply technology that deals with chelators of specific drugs. Moreover, N. G. M. Schipper et al. report that chitosan, which are cationic natural polymers, have drug absorption-promoting effects as a tight-junction opener of the digestive tract mucous membrane in tests using Caco-2 cells. Nevertheless, it is reported that chitosan reduce drug permeability by interaction with the mucous layer in tests using HT-29 cells in vitro, and they do not improve oral absorption by preventing interaction between a drug and components of the mucous layer and mucous membrane of the digestive tract (Eur. J. Pharm. Sci., 8, No. 4, pp. 335-343, 1999).

On the other hand, aminoalkyl methacrylate copolymer E is a copolymer of methyl methacrylate and butyl methacrylate and dimethylaminoethyl methacrylate that was developed by Röhm, and is a polymer substance marketed under the brand name of Eudragit™ E100 or Eudragit™ EPO (both by Röhm GmbH).

Aminoalkyl methacrylate copolymer E is a famous film coating base that is commonly used to mask the bitter taste and color of tablets and granules and provide moisture resistance, etc., having the properties of (1) quickly dissolving in gastric juices and (2) dissolving in buffer with a pH of 5.0 or lower and expanding film in buffer at a pH of 5.0 or higher. Consequently, in addition to masking the bitter taste and color of drugs and providing moisture resistance, aminoalkyl methacrylate copolymer E is being used for solubilization of drugs, etc.

Moreover, aminoalkyl methacrylate copolymer E is used as a base that forms a solid dispersion in order to increase solubility of slightly soluble drugs.

Nevertheless, the fact that oral absorptivity is improved when aminoalkyl methacrylate copolymer E enhances permeability of drugs in the digestive tract mucous membrane and/or mucous layer was not known at all in the past.

In addition, aminoalkyl methacrylate copolymer E is a gastrosoluble polymer base and therefore, it has not been used to make pharmaceutical preparations by being mixed with acidic substances, which would degrade this function.

Incidentally, the following methods are known as technology for using aminoalkyl methacrylate copolymer E to improve oral absorption of drugs:

An invention relating to a solid dispersion consisting of 4"-O-paramethoxyphenylacetyl)tyrosine antibiotic and acrylic polymer copolymer, such as aminoalkyl methacrylate copolymer E, etc., is disclosed in EP 413,299 (corresponds to Japanese Kokai Patent No. Hei 3-74396).

Moreover, an invention pertaining to a method of producing a solid dispersion of a slightly soluble drug comprising this drug and aminoalkyl methacrylate copolymer E using a biaxial extruder is disclosed in U.S. Pat. No. 5,456,923.

Nevertheless, these technologies only increase solubility of a drug and as a result, improve oral absorption by making the above-mentioned dispersion. They do not use the function of aminoalkyl methacrylate copolymer E of improving digestive tract absorption of drugs in the mucous layer and mucous membrane of the digestive tract.

In addition, these patent gazettes do not disclose or suggest technology that realizes excellent absorption from the mucous layer and mucous membrane of the digestive tract by uniformly mixing aminoalkyl methacrylate copolymer E and acidic substance.

An invention whereby a core comprising the acid addition salt of a basic drug is coated by a compound of weak alkalinity to bring pH to the neutral or alkaline region where drug solubility is good and as a result, bitter taste is improved and drug absorptivity is improved, and aminoalkyl methacrylate copolymer E is used as the coating agent and binder is disclosed in Japanese Kokai Patent No. Hei 4-327529.

Nevertheless, this technology does not use the function of aminoalkyl methacrylate copolymer E of improving absorptivity from the mucous layer and mucous membrane of the digestive tract.

In addition, this patent gazette dose not disclose technology by which improvement to realize excellent absorption from the mucous layer and mucous membrane of the digestive tract by uniformly mixing aminoalkyl methacrylate copolymer E and acidic substance.

DISCLOSURE OF THE INVENTION

As a result of performing intense studies for the purpose of developing oral pharmaceutical preparations of incadronate and minodronic acid, which are known as third-generation bisphosphonates, under this type of technical standards, the inventors knew that as with other conventional bisphosphonates, these bisphosphonate compounds are difficult to absorb through the digestive tract. They discovered that the reason for this is that these compounds and the metal ions contained in food that is consumed form insoluble complexes, or insoluble complexes are formed with the mucus components of the digestive tract, particularly bivalent metal ions such as calcium ions, and as a result, these compounds become difficult to absorb through the digestive tract. Therefore, the inventors performed intense research of substances that improve absorbtivity of bisphosphonate compounds in the mucous layer and as a result, they found to their complete surprise that the aminoalkyl methacrylate copolymer E used as a film coating base for gastrosoluble polymers or as a polymer base for solid dispersions in conventional oral pharmaceutical preparations will permeate the mucous layer and will permeate the mucous membrane without forming insoluble complexes when present together with these bisphosphonate compounds in the digestive tract.

As a result of further investigation of the causes of this phenomenon, the inventors further discovered that what is particularly surprising is that the function of aminoalkyl methacrylate copolymer E as an agent for improving oral absorption by enhancing drug permeability through the digestive tract mucous layer and/or mucous membrane is not limited to drugs that are difficult to absorb that form insoluble complexes with bivalent metal ions such as calcium ions, etc., including bisphosphonate compounds, etc., or that interact with components of the mucous layer and mucous membrane. It also improves absorption of drugs that are ordinarily absorbed.

Although the details of the reasons for this phenomenon remain unknown, it appears that by reaching the mucous layer and/or mucous membrane before permeation of the drug, the aminoalkyl methacrylate copolymer E in solution form prevents the components contained in these from interacting with the drug and inhibits the formation of insoluble complex, or delays the formation of this complex, or the aminoalkyl methacrylate copolymer E reacts directly with the digestive tract mucous membrane, leading to enhanced drug permeability of the epithelial cells and/or spaces between cells.

From this viewpoint, the inventors performed further intense studies of pharmaceutical compositions with which improved absorption in the mucous layer and/or mucous membrane of the digestive tract can be realized and as a result, discovered that using aminoalkyl methacrylate copolymer E, which thus far has not been used to make pharmaceutical preparations by being uniformly mixed with an acidic substance, drug, and acidic substance as the essential components of the mixture, it is possible for these substance to reach the mucous layer and/or mucous membrane of the digestive tract in solution form by bringing said mixture components together and uniformly mixing preferably these 3 components, or at least the aminoalkyl methacrylate copolymer E and acidic substance, and that oral absorptivity of various drugs is markedly improved.

The present invention was completed based on these discoveries.

That is, the present invention presents 1. a pharmaceutical composition for oral use with improved absorption, which comprises drug, aminoalkyl methacrylate copolymer E, and acidic substance and which is made by bringing said 3 components together and uniformly mixing at least the above-mentioned polymer and above-mentioned acidic substance, 2. the pharmaceutical composition of above-mentioned 1, wherein the drug, aminoalkyl methacrylate copolymer E, and acidic substance are uniformly mixed, 3. the pharmaceutical composition of above-mentioned 1 or 2, wherein the amount of aminoalkyl methacrylate copolymer E that is added is 0.01 part by weight or more per 1 part by weight of drug, 4. the pharmaceutical composition of any one of above-mentioned 1 through 3, wherein the acidic substance is one where when 1 g of said substance is dissolved in 50 ml water, pH of said solution is brought to 6 or lower, 5. the pharmaceutical composition of any one of above-mentioned 1 through 4, wherein the amount of acidic substance added is the amount that will neutralize 10% or more of basic groups of aminoalkyl methacrylate copolymer E, 6. the pharmaceutical composition of any one of above-mentioned 1 through 5, comprising 0.05~500 parts by weight of aminoalkyl methacrylate copolymer E per 1 part by weight of drug in the effective amount for treatment or prevention of disease, and acidic substance in the amount that will neutralize 10% or more of the basic groups of the above-mentioned polymer, 7. the pharmaceutical composition of any one of above-mentioned 1 through 5, comprising 0.05~500 parts by weight of aminoalkyl methacrylate copolymer E per 1 part by weight of drug in the effective amount for treatment or prevention of disease, and 0.005~50 parts by weight of acidic substance per 1 part by weight of the above-mentioned polymer, 8. the pharmaceutical composition of any one of above-mentioned 1 through 7, wherein the aminoalkyl methacrylate copolymer E and acidic substance are granulated, 9. the pharmaceutical composition of any one of above-mentioned 1 through 7, wherein the aminoalkyl methacrylate copolymer E and acidic substance are dissolved in a pharmaceutically acceptable solvent and/or after dissolution, said substance is spray dried to obtain a spray-dried substance, or said solution is lyophilized to obtain a lyophilized substance, 10. the pharmaceutical composition of any one of above-mentioned 1 through 7, wherein the aminoalkyl methacrylate copolymer E and acidic substance are in a state of dissolution and/or suspension in a pharmaceutically acceptable solvent, 11. the pharmaceutical composition of any one of above-mentioned 1 through 10, wherein the form of the pharmaceutical preparation is 1 or 2 or more selected from the group consisting of granules, tablets, capsules, and liquid, 12. the pharmaceutical composition of any one of above-mentioned 1 through 11, wherein the drug is a drug that is difficult to absorb, 13. the pharmaceutical composition of above-mentioned 12, wherein the drug is a bisphosphonate compound, 14. a method of improving oral absorption of a drug by using a pharmaceutical composition obtained by bringing drug, aminoalkyl methacrylate copolymer E, and acidic substance together and uniformly mixing at least the above-mentioned polymer and acidic substance, 15. the method of above-mentioned 14, wherein a pharmaceutical composition obtained by uniformly mixing drug, aminoalkyl methacrylate copolymer E, and acidic substance is used, 16. the method of above-mentioned 14 or 15, wherein the aminoalkyl methacrylate copolymer E is used in the amount of 0.01 parts by weight or more per 1 part by weight of drug, 17. the method of any one of above-mentioned 14 through 16, wherein the acidic substance that is used is one with which when 1 g of said substance is dissolved in 50 ml water, pH of said solution is brought to 6 or lower, 18. the method of any one of above-mentioned 14 through 17, wherein the acidic substance is used in the amount that will neutralize 10% or more of the basic groups of aminoalkyl methacrylate copolymer E, 19. the method of any one of above-mentioned 14 through 18, wherein pharmaceutical composition is used which comprises 0.05~500 parts by weight of aminoalkyl methacrylate copolymer E in terms of 1 part by weight of drug in the amount effective to treat or prevent disease, and acidic substance in an amount that will neutralize 10% or more of basic groups of the above-mentioned polymer, 20. the method of any one of above-mentioned 14 through 18, wherein a pharmaceutical composition is used which comprises 0.05~500 parts by weight of aminoalkyl methacrylate copolymer E per 1 part by weight of drug in an effective amount for treatment or prevention of disease, and 0.005~50 parts by weight of acidic substance per 1 part by weight of the above-mentioned polymer, 21. the method of any one of above-mentioned 14 through 20, wherein a composition is used in which the aminoalkyl methacrylate copolymer E and acidic substance are granulated, 22. the method of any one of above-mentioned 14 through 20, wherein the aminoalkyl methacrylate copolymer E and acidic substance are dissolved in a pharmaceutically acceptable solvent and/or used as a spray-dried substance that has been obtained by spray drying said solution or used as a lyophilized substance that has been obtained by lyophilization of said solution, 23. the method of any one of above-mentioned 14 through 20, wherein the aminoalkyl methacrylate copolymer E and acidic substance are used in a state of dissolution and/or suspension in a pharmaceutically acceptable solvent, 24. the method of any one of above-mentioned 14 through 23, wherein the form of the pharmaceutical preparation is 1 or 2 or more selected from the group consisting of granules, tablets, capsules, and liquid, 25. the method of any one of above-mentioned 14 through 24, wherein drug that is difficult to absorb is used as the drug, 26. the method of above-mentioned 25, wherein a bisphosphonate compound is used as the drug, 27. an agent for improving oral absorption by increasing drug permeability of the digestive tract mucous membrane and/or the mucus layer distributed over this mucous membrane, whose active ingredient is aminoalkyl methacrylate copolymer E, 28. the agent for improving oral absorption of above-mentioned 27 by the effect of inhibiting the formation and/or the effect of delaying the formation of insoluble complex based on interaction between the drug and the digestive tract mucous layer and/or digestive tract mucous membrane, 29. the agent that promotes oral absorption of above-mentioned 27 or 28, which is used in the presence of acidic substance, 30. the use of aminoalkyl methacrylate copolymer E as an agent for improving oral absorption that enhances drug permeability of the digestive tract mucous membrane and/or mucus layer distributed over this mucous membrane, 31. the use of above-mentioned 30, wherein aminoalkyl methacrylate copolymer E is used as an agent for improving oral absorption having the effect of inhibiting the formation and/or the effect of delaying the formation of an insoluble complex based on the interaction between a drug and the digestive tract mucous layer and/or digestive tract mucous membrane, 32. The use of above-mentioned 31, which is used in the presence of an acidic substance.

The "digestive tract" in the present specification means the small intestine consisting of the duodenum, jejunum, and ileum, as well as the large intestine consisting of the colon, the ascending colon, transverse colon, descending colon, sigmoid colon, and the rectum.

The term "bring together" in the present specification means the state where each component of drug, aminoalkyl methacrylate copolymer E and acidic substance is present close to one another in a solid or liquid state. Moreover, the general idea of "bring together" also includes the state where each component contacts one another. Furthermore, there are no special restrictions with respect to the state of the drug, and it can be used as is or can be pre-treated. When stability drops as a result of a drug making contact with acidic substance, etc., the drug is used, for instance, in a pre-treated state (for instance, the state of being coated by a water-soluble substance, such as sugar, starch, hydroxypropylmethyl cellulose, etc.), and in this case, the state of treated drug and above-mentioned components being present close to one another or contacting one another is also included in the general concept of "bring together." In addition, "state of being present close to one another" means that state where each component is present to such an extent that the purpose of the present invention is realized, making it possible to improve drug permeability of the digestive tract mucous layer and/or mucous membrane and improve oral absorption.

The term "at least" in the present specification means the 2 components of aminoalkyl methacrylate copolymer E and acidic substance, or the 3 components of drug, aminoalkyl methacrylate copolymer E, and acidic substance.

The term "uniformly" in the present specification means the state where each component of drug, aminoalkyl methacrylate copolymer E, and acidic substance is uniformly dispersed and present as a whole, that is, the state where there is no misdistribution. For instance, the state where there is misdistribution of any of the components as in the case of 3-layer tablets where drug, aminoalkyl methacrylate copolymer E and acidic substance are each layered, etc., is not included in "uniformly." Moreover, "uniformly mixed" is the state of being mixed by methods known in the field of pharmaceutical preparations, and an example is a solid composition produced by physical mixing, spray drying, lyophilization, or granulation (wet granulation, dry granulation) of each component, or a liquid composition where each component is suspended and/or dissolved in a pharmaceutically acceptable solvent, such as water, etc. FIG. 1 shows some of the embodiments, but [the present invention] is not limited to these embodiments.

First, the novel use of the present invention will be described.

The present invention pertains to an agent for improving oral absorption by enhancing drug permeability in the digestive tract mucous membrane and/or the mucous layer distributed over this mucous membrane whose effective component is aminoalkyl methacrylate copolymer E.

The use of the present invention is characterized in that oral absorption of drugs is improved by the effect of inhibiting reduction of drug permeability of the mucous layer, and the effect of inhibiting and/or the effect of delaying the formation of insoluble complex, etc., based on interaction between components of the mucous layer and/or mucous membrane of the digestive tract and drugs, of aminoalkyl methacrylate copolymer E.

The pharmaceutical composition for oral use with [improved] absorption of the present invention will now be described:

The pharmaceutical composition of the present invention is characterized in that aminoalkyl methacrylate copolymer E and acidic substance are uniformly mixed, and in that acidic substance in an amount that will neutralize 10% or more of the basic groups of this polymer is uniformly mixed with this polymer. The pharmaceutical composition that is obtained by uniformly mixing both substances has advantageous effects in that (1) this polymer can be dissolved, even at neutral sites or sites of weak alkalinity in the digestive tract and therefore, it is possible to improve absorption of drugs with which in the past there was apparently a reduction in oral absorption because an insoluble complex (for instance, complexes based on interaction with each biological component present in the digestive tract, digestive tract mucous layer or digestive tract mucous membrane) (for example, insoluble complex, such as a complex based on interaction with metal ions, including calcium ions, magnesium ions, etc., or with biologically secreted components, such as bile acids, etc.) is formed inside the digestive tract, (2) the optimum absorption site generally varies with the type of drug and therefore, a pharmaceutical preparation design that takes into consideration the optimal absorption site is necessary, but aminoalkyl methacrylate copolymer E can be dissolved of course in the small intestine with a large effective absorption surface area, including the duodenum of the upper small intestine and the jejunum and ileum, etc., as well as in the colon, including the ascending colon, transverse colon, descending colon, and sigmoid colon, and rectum, etc., of the lower digestive tract with a low water content, and as a result, the entire digestive tract becomes the effective absorption site of the drug, (3) a reduction in drug permeability of the mucous layer based on interaction between the components of the mucous layer and/or mucous membrane of the digestive tract can be inhibited by aminoalkyl methacrylate copolymer E, (4) oral absorption of a drug can be improved by the effect of inhibiting and/or the effect of delaying the formation of insoluble complex, etc.

There are no particular restrictions to the drug used in the present invention as long as it is one used as a pharmaceutically active component for treatment or prevention of disease. Examples of this drug are drugs that are difficult to absorb because of interaction with the digestive tract mucous layer and/or mucous membrane, such as drugs that are difficult to absorb from the digestive tract because permeability of the mucous layer present on the digestive tract mucous membrane is poor, drugs that are difficult to absorb due to interaction with substances present in the mucous layer, drugs that are difficult to absorb because of poor permeability of the digestive tract mucous membrane, etc., or drugs that are difficult to absorb because they form insoluble complexes with bile acids. Moreover, in addition to the above-mentioned drugs that are difficult to absorb, the drugs used in the present invention include all drugs that are normally absorbed. For instance, natural extracts derived from flora and fauna (for instance, extracts, tinctures, etc.), or compounds isolated from extracts, etc., or compound that have been chemically synthesized, etc., are included in the present invention. The drug can be a single component, or it can be a mixture of two or more components. In addition, when the drug is a compound, salts of compounds, various solvates of these compounds that are pharmaceutically acceptable (for instance, water, etc.), and solvates of salts of these compounds are included in the present invention. Moreover, their crystal polymorphs are also included. When asymmetric carbons are found in the structure of the compound and there are optical isomers or stereoisomers of the compound, these optical isomers, stereoisomers, and mixtures of these isomers are all included in the present invention. There are no particular restrictions to the salt of the compound as long as it is one that is pharmaceutically acceptable. Specific examples are mineral acid salts of hydrochlorides, hydrobromides, hydroiodides, phosphates, nitrates, sulfates, etc., organic sulfonates, such as methanesulfonates, ethanesulfonates, 2-hydroxyethanesulfonates, p-toluenesulfonates, etc., organic carboxylates, such as acetates, propionates, oxalates, malonates, succinates, glutarates, adipates, tartrates, maleates, malates, mandelates, etc., and the like.

The drug used in the present invention can be an osteoporosis drug, a bone metabolism-improving agent, a hypnotic sedative, a sleep-inducing agent, an anti-anxiety agent, an anti-epilepsy agent, an antidepressant, an anti-Parkinson's agent, an agent used for the treatment of psychoneurosis, an agent used for the treatment of central nervous system disorders, a local anesthetic, a skeletal muscle relaxant, an agent used for the treatment of autonomic nervous system disorders, an anti-inflammatory antipyretic analgesic, a spasmolytic, an anti-vertigo agent, a cardiotonic, an agent for the treatment of arrhythmia, a diuretic, a hypotensive, a vasoconstrictor, a vasodilator, a drug for treatment of circulatory disorders, an agent for hyperlipidemia, an agent that promotes respiration, an antitussive, an expectorant, an antitussive expectorant, a bronchodilator, an antidiarrheal agent, an agent for controlling intestinal function, an agent for treatment of peptic ulcers, a stomachic, an antacid, a laxative, a cholagogue, a gastrointestinal drug, an adrenocortical hormone, a hormone, an agent for treatment of urogenital disorders, a vitamin, a hemostatic, an agent for treating liver disease, an agent for treatment of gout, an agent for treatment of diabetes, an antihistamine, an antibiotic, an antibacterial, an anti-malignant tumor agent, a chemotherapeutic agent, a multisymptom cold agent, a nutrition-enhancing health agent, etc. Examples are bisphosphonate compounds (incadronate, ((cycloheptylamino)-methylene)bis-phosphonate), YM175; produced by the method in Japanese Patent No. Hei 7-629 (corresponds to U.S. Pat. No. 4,970,335)), minodronic acid ([1-hydroxy-2-imidazo(1,2-a)pyridin-3-ylethylidene]bis-phosphonate), YM529; produced by the method entered in Japanese Patent No. Hei 6-99457), alendronate (4-amino-1-hydroxybutylidene 1,1-bisphosphonate produced by the method in U.S. Pat. Nos. 4,922,007, 5,019,651, 5,510,517, 5,648,491), ibandronate, etidronate ((1-hydroxyethylidene)-1,1-bisphosphonate), olpadronate, chlodronate, zoledronate, tiludronate, neridronate, pomegranate, risedronate, [1-hydroxy-3-(1-pyrrolidinyl)-propylidene]bis-phosphonate, etc.), 5-aminosalicylic acid, acyclovir, adinazolam, ascorbic acid, aspirin, acetylsalicylic acid, acetaminophen, acetobutol, acetohexamide, atenolol, atorvastatin, apomorphine, aminopyrine, aminophylline, ethyl aminobenzoate, amrinone, amobarbital, albuterol, alprazolam, allopurinal, ampicillin, ambroxole, isoniazide, idebenone, ibuprofen, imipramine, indeloxazine, indomethacin, idenzamide, ethosuccimide, etomidoline, enalapril, ephedrine, erythromycin, oxytetracycline, oxyphenbutazone, osalazine, omeprazole, carmofur, quinidine, quinine, griseofulvin, glibizide, glucagon, glibenclamide, chloramphenicol, chlordiazepoxide, chlorthiazide, ketoconazole, colestimide, codeine, cobamamide, colchicine, zafirlukast, diazepam, digitoxin, diclofenac, diclofenac sodium, cyclophosphamide, digoxin, cycotiamine, dipyridamole, cimetidine, josamycin, sinvastatin, sucralfate, scopolamine, spironolactone, sulpiride, sulfasalazine, sulfadimethoxine, sulfamethizole, sulfaguanidine, sulfamethoxazole, sulfisoxazole, cefotatan, cefuroxime, selegiline, celecoxib, tasosartan, thiotepa, theophylline, dextromethorphan, tetracycline, tepronone, terfenadine, terbutaline, doxorubicin, tramadole, etodolac, triamcinolone, triamterene, torbutamide, nateglinide, nadolol, naproxen, nicotinamide, nitroglycerin, nitrofurantoin, nifedipine, nemonapride, noscapine, hydrocortisone, pafenolol, vardecoxib, sodium valproate, haloperidol, hydrochlorothiazide, hydrocortisone, pilocarpine, faropenem sodium, famotidine, phenacetin, phenyloin, phenylbutazone, phenyl propanolamine, phenobarbital, fenoprofen calcium, pseudoephedrine, budesonide, formoterol fumarate, praunotol, pravastatin, pravastatin sodium, pranrucast, purimidone, fluorouracil, predinisoline, prednisone, procainamide, prostaglandine I derivative, such as beraprost sodium, etc., furosemide, probenecide, bromovaleryl urea, betamethazone, penicillin, peroxetin, perfphenazine, benzyl penicillin, pentazocine, calcium homopanthothenate, polythiazide, chlorophenylamine maleate, midazolam, milnacipran, doxazocin mesilyate, methyl dopa, methylphenidate, methoclopramide, methotrexate, methoprolol, mepirizole, morphine, ranitidine, lamsoprazole, lisinopril, resperidone, riseofulvin, lidocaine, codeine phosphate, dimemorphan phosphate, pyridoxal phosphate, levonorgesterol, reserpine, levo dopa, lovastatin, lorazepam, warfarin, aclarubicin hydrochloride, azasetron hydrochloride, amitriptyline hydrochloride, amosulalol hydrochloride, ampicillin phthalizyl hydrochloride, indenolol hydrochloride, ethambutol hydrochloride, ondansetron hydrochloride, granisetron hydrochloride, chloropromazine hydrochloride, diphenhydramine hydrochloride, dibucaine hydrochloride, tamsulasin hydrochloride, thiapride hydrochloride, terazosine hydrochloride, nicardipine hydrochloride, barnidipine hydrochloride, hydralazine hydrochloride, bifemerane hydrochloride, prazosin hydrochloride, propafenone hydrochloride, moperone hydrochloride, ranitidine hydrochloride, ramosetron hydrochloride, butyl scopolamine bromide, isosorbid nitrate, quinidine nitrate, guanetidine nitrate, thiamine nitrate, tocopherol acetate, chloral hydrate, etc. In addition to bisphosphonate, the "bisphosphonate compounds" in the present Specification include bisphosphonic acid, diphosphonate, diphosphonic acid, and their pharmaceutically acceptable salts, as well as their derivatives. Examples of pharmaceutically acceptable salts are 1 or 2 or more selected from the group consisting of alkali metal salts, alkali earth metal salts, ammonium salts, and ammonium salts substituted by mono-, di-, tri-, or tetra-alkyl (1~30 carbons). Specific salts are preferably 1 or 2 or more selected from the group consisting of sodium salt, potassium salt, calcium salt, magnesium salt, and ammonium salt. The drug used in the present invention is preferably a bisphosphonate compound. Of these, incadronate, minodronic acid, alendronate, and ethidronate are preferred, and incadronate and minodronic acid are ideal.

Peptides, proteins, and their derivatives are also examples of the drug used in the present invention. Examples are insulin, calcitonin, angiotensin, vasopressin, desmopressin, LH-RH (leutinizing hormone releasing hormone), somostatin, glucagon, oxytocin, gastrin, cyclosporin, somatomedin, secretin, h-ANP (human atrial natriuretic peptide), ACTH (adrenocorticotropic hormone), MSH (melanophore-stimulating hormone), β-endorphin, muramyl dipeptide, enkephalin, neurotensin, bombesin, VIP (vasoactive intestinal peptide), CCK-8 (cholecystokinin-8), PTH (parathyroid hormone), CGRP (calcitonin gene-related peptide), TRH (thyrotropin-releasing hormone), encloserin, hGH (human growth hormone), cytokines, such as interleukin, interferon, colony-stimulating factor, tumor necrosis factor, etc., and derivatives of the same, etc. These peptides and proteins include not only those naturally derived, but also their pharmacologically active derivatives and their homologs. For instance, natural calcitonin, such as salmon calcitonin, human calcitonin, pork calcitonin, eel calcitonin, and chicken calcitonin, etc., as well as their homologs, such as their genetic recombinants, etc., are included in the calcitonin that is the subject of the present invention. Moreover, the insulin includes human insulin, pork insulin, etc., as well as homologs of the same, such as their genetic recombinants, etc.

In the case of peptides and proteins, a pharmaceutical preparation for oral use can be presented as long as preparation technology is used whereby this drug is delivered to the lower part of the digestive tract, such as the jejunum, ileum, colon, and large intestine, etc., where digestive enzymes have little effect without being decomposed. Examples of this preparation technology are sustained-release pharmaceutical preparations (refer to International Publication Pamphlet WO94/06414, for instance), colon-released pharmaceutical preparation (refer to International Publication Pamphlet WO95/28963 for instance), timed-release or pulsed-release pharmaceutical preparation (refer to the post-script of PCT/JP01/03229 (filed on Apr. 16, 2001)/U.S. Ser. No. 09/834,410 (filed on Apr. 12, 2001), and International Publication Pamphlet 93-05771, for instance), etc.

As previously mentioned, in addition to drugs that are difficult to absorb, all drugs that are normally absorbed are included among the drugs of the present invention. Drugs with which the pharmacological effect in clinical terms is realized by administration of large doses orally, even though they are difficult to absorb due to interaction with the digestive tract mucous membrane and/or mucous layer, interaction with bile acids, etc., are included among drugs that are usually absorbed. The pharmacological effect that is clinically expected can be realized with a smaller dose when the present invention is applied to these drugs and therefore, a reduction in adverse effects due to the large doses administered in the past can be expected.

There are no special restrictions to the amount of drug used in the present invention as long as it is the effective amount in terms of treatment or prevention of disease.

There are no particular restrictions to the state of the aminoalkyl methacrylate copolymer E when it is mixed in the pharmaceutical composition of the present invention as long as it is brought together with the drug and is uniformly mixed with acidic substance, which is described later. This state can be, for instance, a solid, such as a powder of this polymer itself, or a liquid, such as an aqueous solution of this polymer suspended and/or dissolved in water. Moreover, conventional methods such as crushing, spray drying, lyophilization, wet granulation, dry granulation, etc., can be used as the method for making a powder. It is preferred that acidic substance, which is mentioned later, be added as the dissolution auxiliary agent for this polymer. The aminoalkyl methacrylate copolymer E can have free amino groups and can be a soluble salt. The preferred embodiment in the case of soluble salts is preparation by spray drying or lyophilization of a solution of aminoalkyl methacrylate copolymer E dissolved, or dissolved and suspended, together with acid. The aminoalkyl methacrylate copolymer E can contain surfactant. There are no special restrictions to the surfactant that is added as long as it is usually pharmaceutically acceptable and it reduces water repellency of this polymer. Nonionic surfactants (for instance, polyoxyethylene surfactants (such as polysorbate 80, polyoxil stearate 40, lauroMacrogol, polyoxyethylene-hydrogenated castor oil (HCO-60), sucrose fatty acid ester, etc.)), ionic surfactants (anionic surfactants (for instance, sodium laurylsulfate, etc.), cationic surfactants (for instance, benzalconium chloride, etc.), amphoteric surfactants (lecithin, etc.)), etc., are examples. One or a mixture of 2 or more as needed can be used. There are no special restrictions to the amount of surfactant added as long as it is an amount that will reduce water repellency of this polymer, but it is usually approximately 0.01~10 parts by weight, preferably approximately 0.01 to 5 parts by weight, further preferably approximately 0.05~1 part by weight, per 1 part by weight of this polymer. There are no special restrictions to the solvent in which the aminoalkyl methacrylate copolymer E (containing surfactant when needed) is dissolved or suspended as long as it is a solvent that is usually pharmaceutically acceptable. Examples are water, organic solvent (for instance, methanol, ethanol, isopropanol, acetone, etc.), mixtures of water and organic solvent, etc. Moreover, the pharmaceutical composition of the present invention can also contain various fillers that are used as pharmaceutical additives and other additives. Extenders such as lactose, starch, etc., can also be added as the filler or additive.

There are no special restrictions to the amount of aminoalkyl methacrylate copolymer E used in the present invention as long as the relationship with the amount of drug added is adjusted as needed. It is usually 0.01 part by weight or more, preferably 0.05~500 parts by weight, further preferably 0.1~250 parts by weight, particularly 0.5~50 parts by weight, per 1 part by weight of drug. Incidentally, surfactant can also be mixed with the aminoalkyl methacrylate copolymer E for the purpose of promoting absorption even further. Nonionic surfactants (for instance, polyoxyethylene surfactants (such as polysorbate 80, polyoxil stearate 40, lauroMacrogol, polyoxyethylene-hydrogenated castor oil (HCO-60), sucrose fatty acid ester, etc.), ionic surfactants (anionic surfactants (for instance, sodium laurylsulfate, etc.), cationic surfactants (for instance, benzalconium chloride, etc.), amphoteric surfactants (lecithin, etc.)), etc., are examples. One or a mixture of 2 or more as needed can be used.

There are no special restrictions to the acidic substance used in the present invention as long as it is pharmaceutically acceptable and capable of dissolving the aminoalkyl methacrylate copolymer E by neutralizing some or all of the basic groups of this polymer in the presence of water. An inorganic acid and/or organic acid with which pH of a solution of 1 g of this acidic substance dissolved or dispersed in 50 ml of water is 6 or less is preferred as this acidic substance. Examples of the acidic substance used in the present invention are inorganic acids, such as hydrochloric acid, phosphoric acid, potassium dihydrogen phosphate, sodium dihydrogen phosphate, etc., organic acids such as citric acid, lactic acid, tartaric acid, fumaric acid, phthalic acid, acetic acid, oxalic acid, malonic acid, adipic acid, phytic acid, succinic acid, glutaric acid, maleic acid, malic acid, mandelic acid, ascorbic acid, benzoic acid, methanesulfonic acid, capric acid, capronic acid, caprylic acid, lauric acid, arachidonic acid, erucic acid, linoleic acid, linolenic acid, oleic acid, palmitic acid, myristic acid, stearic acid, etc.; aspartic acid, L-glutamic acid, L-cystein, arginine hydrochloride, lysine hydrochloride, L-glutamic acid hydrochloric acid salt, etc. One or a combination of 2 or more of these can be used.

There are no special restrictions to the amount of acidic substance used in the present invention as long as it is an amount capable of dissolving the aminoalkyl methacrylate copolymer E by neutralizing some or all of the basic groups of this polymer in the presence of water. The amount of this substance that is added is the amount that will neutralize usually approximately 10% or more, preferably approximately 15% or more, further preferably approximately 30% or more, particularly approximately 40% or more, ideally 50% or more, of the basic groups of this polymer. The presence of 50% or more acidic substance is ideal because the spray-dried product can be easily handled during production without any aggregation, even when stored for a long period of time. The amount of this acidic substance is adjusted as needed taking into consideration solubility and/or acidity of this substance, but it is usually 0.005~50 parts by weight, preferably 0.01~30 parts by weight, particularly 0.03~10 parts by weight, per 1 part by weight aminoalkyl methacrylate copolymer E. Furthermore, when 312.5 g of 1 mola hydrochloric acid per 500 g Eudragit E, for instance, is added as the acidic substance used in the present invention and spray dried, calculation can be by the following formula (I):

$$\frac{1 \times 312.5}{1000} \text{ (Number of moles of hydrochloric acid)} = \frac{X}{KOH(56)} \times \text{Number of moles of } KOH \quad \text{Formula (I)}$$

X=17.49 g, but because it is the amount in 500 g, divide by 500.

X/1 g Eudragit E=35 mg KOH

Actually, since the alkali value in 1 g Eudragit E is 163-198 mg KOH, the amount of acid added at this time was 15~20% the amount that would neutralize all of the alkali.

There are no particular restrictions to the uniform mixing of the aminoalkyl methacrylate copolymer E and acidic substance used in the present invention as long as it is a state wherein they are brought together with the drug and uniformly mixed and the embodiment can be used whereby aminoalkyl methacrylate copolymer E can be dissolved by acidic substance in the presence of water. A state wherein drug, this polymer and this acidic substance are uniformly mixed is preferred. The embodiment whereby they are mixed by conventional methods is an example of this state. For instance, the embodiment whereby aminoalkyl methacrylate copolymer E prepared by the method described previously by mixing the above-mentioned aminoalkyl methacrylate copolymer E, or liquid of aminoalkyl methacrylate copolymer E and acidic substance, or aminoalkyl methacrylate copolymer E and acidic substance dissolved and/or suspended in a pharmaceutically acceptable solvent (for instance, water, alcohol (methyl, ethyl, propyl, butyl, etc.) or their mixtures, etc.) together with drug, is made into a powder by conventional methods, such as spray drying, etc., the embodiment whereby aminoalkyl methacrylate copolymer E and acidic substance are mixed by conventional methods or are granulated to make a mixture, the embodiment whereby a liquid of aminoalkyl methacrylate copolymer E and acidic substance dissolved and/or suspended in a solvent that is pharmaceutically acceptable, the embodiment whereby drug is further added in the above-mentioned embodiment, etc., are given. There are no particular restrictions to the pharmaceutical composition that can be specifically used in these embodiments as long as it is in a form that can be orally administered as a pharmaceutical preparation. This preparation can be for instance, a powder, tablets, capsules, a liquid, a suspension, an emulsion, or capsules, etc., filled with a liquid, a suspension, an emulsion, etc.

The method of producing this pharmaceutical preparation can be a conventional method. Specific examples of this preparation are solution/suspension of aminoalkyl methacrylate copolymer E and acidic substance dissolved and/or suspended in pharmaceutically acceptable solvent, capsules wherein the above-mentioned solution/suspension is filled in capsules, such as gelatin capsules, mixture obtained by mixing aminoalkyl methacrylate copolymer E and acidic substance by conventional methods and then mixing this mixture with drug, granules obtained by mixing aminoalkyl methacrylate copolymer E and acidic substance, adding a solvent that is pharmaceutically acceptable, such as water, etc., adding a binder such as hydroxypropoyl methyl cellulose, etc., as needed and granulating the product, tablets obtained by mixing pharmaceutical filler with the above-mentioned mixture or granulated product and then tableting, capsule preparation of the above-mentioned granules filled in, for instance, gelatin capsules, enteric-coated preparation obtained by coating the above-mentioned granules with an enteric substance (for instance, 1:1 copolymer of methyl methacrylate and methacrylic acid (brand name Eudragit™L, Röhm GmbH), 2:1 copolymer of methyl methacrylate and methacrylic acid (brand name Eudragit™S, Röhm GmbH), 1:1 copolymer of ethyl acrylate and methacrylic acid (brand name: Eudragit™ LD-55, Röhm GmbH), hydroxypropyl methyl cellulose phthalate, hydroxypropyl methyl cellulose acetate succinate, carboxymethyl ethyl cellulose, cellulose acetate phthalate, shellac, zein, etc., or enteric-coated preparation obtained by coating tablets obtained by tableting the above-mentioned granules with enteric substance (same as the above-mentioned). The preparations can be made by conventional methods. In this case, pharmaceutical additives, such as fillers, disintegrators, binders, lubricants, fluidizers, dispersants, suspension agents, emulsifiers, preservatives, stabilizers, etc., can be added to the pharmaceutical composition of the present invention as needed.

The mixture ratio of drug, aminoalkyl methacrylate copolymer E and acidic substance contained in the pharmaceutical composition is 0.05~500 parts by weight (preferably 0.1~250 parts by weight, further preferably 0.5~50 parts by weight) of aminoalkyl methacrylate copolymer E per 1 part by weight drug in the amount effective in terms of treatment or prevention of disease, and the amount of acidic substance that will neutralize 10% or more (preferably 15% or more, further preferably 30% or more, particularly 40% or more, ideally 50% or more) of the basic groups of the above-mentioned polymer. The mixture ratio can be selected by using an appropriate combination from the preferred combination ratio for each component, but of these, the preferred mixture ratio is 0.5~50 parts by weight of aminoalkyl methacrylate copolymer E per 1 part by weight drug in the effective amount in terms of treatment or prevention of disease, and acidic substance in an amount that will neutralize 50% or more of the basic groups of the above-mentioned polymer. A combination ratio of the above-mentioned 3 components where there are 0.05~500 parts by weight (preferably 0.1~250 parts by weight, further preferably 0.5~50 parts by weight) of aminoalkyl methacrylate copolymer E per 1 part by weight drug in the amount that is effective in terms of treatment or prevention of disease, and 0.005~50 parts by weight (preferably 0.01~30 parts by weight, further preferably 0.03~10 parts by weight) of acidic substance per 1 part by weight of the above-mentioned polymer in the pharmaceutical composition is also possible. The mixture ratio can be selected by using an appropriate combination from the group of preferred combination ratios of each component. However, of these, the preferred combination ratio is 0.5~50 parts by weight of aminoalkyl methacrylate copolymer E per 1 part by weight of drug in an amount effective for treatment or prevention of disease and 0.03 to 10 parts by weight of acidic substance per 1 part by weight of the above-mentioned polymer.

The pharmaceutical composition for oral use of improved absorption of the present invention can be used in a variety of pharmaceutical preparations as previously described. However, further specific pharmaceutical preparations are sustained-released pharmaceutical preparations (refer to International Publication Pamphlet WO94/06414, for instance), colon-released pharmaceutical preparations (refer to International Publication Pamphlet WO95/28963, for instance), timed-release or pulsed-release pharmaceutical preparation (refer to PCT/JP01/03229 (filed on Apr. 16, 2001), U.S. Ser. No. 09/834,410 (filed on Apr. 12, 2001), International Publication Pamphlet WO93/05771, for instance), microparticle pharmaceutical preparation (refer to Japanese Domestic Publication No. Hei 10-511957, for instance), mucous membrane adhesion-type pharmaceutical preparation (refer to Japanese Kokai Patent No. Hei 5-132416, for instance), etc. The hydrogel-forming sustained-release pharmaceutical preparation described in International Publication WO94/06414, colon-released pharmaceutical preparation (for instance, a pharmaceutical preparation wherein a mixture of granulation product obtained by granulation of the pharmaceutical composition for oral use of improved absorptivity of the present invention and saccharide that is decomposed by intestinal flora to generate organic acid (for instance, lactulose) is coated with polymer substance that is dissolved by organic acid, then is coated with a nonionic substance, such as hydroxypropyl methyl cellulose as needed, and is further coated with enteric substance, or a pharmaceutical preparation wherein tablets obtained by tableting the above-mentioned mixture are coated with polymer substance that is dissolved by inorganic acids, are then coated with a nonionic substance, such as hydroxypropyl methyl cellulose, etc., as needed, and further coated by enteric substance) described in WO95/28963, and timed-release pharmaceutical preparation described in above-mentioned PCT/JP01/03229 (filed on Apr. 16, 2001)/ U.S. Ser. No. 09/834,410 (filed on Apr. 12, 2001) are preferred.

The timed-release pharmaceutical preparation of PCT/JP01/03229 (filed on Apr. 16, 2001)/U.S. Ser. No. 09/834,410 (filed on Apr. 12, 2001) will be described below in detail:

The invention relating to the application in question pertains to timed-release dry-coated tablets, characterized in that they are a hydrogel-forming dry-coated solid pharmaceutical preparation comprising a core containing the drug and an outer layer made from hydrogel-forming polymer and hydrophilic base wherein (1) drug and "readily erodible filler" are mixed in the core, (2) the percentage erosion of the core is approximately 40~approximately 90%, and (3) the outer layer is essentially free of the same drug as the above-mentioned drug.

<Determination of Percentage Erosion>

Dry-coated tablets containing a drug are moistened for 3 hours in water at 37° C. and then the gelled part of the tablet is peeled off and the core that has not eroded is recovered. The core is dried overnight in a dryer at 40° C. and weight is determined. Dry weight is subtracted from the initial core weight and this is divided by the initial core weight. This value is multiplied by 100 to calculate the percentage erosion (%).

There are no special restrictions to the "readily erodible filler" used in the core here as long as it is usually pharmaceutically acceptable and it provides a specific percentage erosion as a pharmaceutical preparation with the combination of drug and other fillers that is used. This filler can be one that itself quickly dissolves in order to quickly erode the core and disperse or dissolve the drug component and/or one that has the ability to quickly dissolve itself and bring pH to one at which the drug will readily dissolve. It is preferred that the filler be selected taking into consideration the physicochemical properties of the drug, particularly whether the drug is an acidic, neutral or basic drug. Examples when the drug is basic are the organic acids of malic acid, citric acid and tartaric acid, and malic acid and citric acid are preferred. Examples when the drug is neutral or acidic are sucrose, polyethylene glycol, lactulose, etc., and sucrose and polyethylene glycol are preferred. In this case, 1 or a mixture of 2 or more fillers can be used. This filler is preferably used as a mixture of 1 or 2 or more selected from malic acid, citric acid, tartaric acid, sucrose, polyethylene glycol, and lactulose.

The amount of this filler that is added can be adjusted taking into consideration the release time that is selected as needed, and is usually approximately 10~approximately 95 wt %, preferably approximately 15~approximately 80 wt % core tablet. Moreover, it is also possible to add 1 or 2 or more additives to the core that are pharmaceutically acceptable for further increasing the bioavailability of a drug in order easily absorb the drug contained in the core, even in the colon where the water content is low. Examples of this additive are surfactants, such as polyoxyethylene-hydrogenated castor oil, polyoxyethylene sorbitane higher fatty acid esters, polyoxyethylene polyoxypropylene glycols, sucrose fatty acid esters, etc. The method of improvement of the properties of the drug itself by means described below are also effective. Specific examples are the method whereby a solid dispersion is formed with a water-soluble polymer, such as hydroxypropyl methyl cellulose, polyvinyl pyrrolidone, polyethylene glycol, etc., or enteric polymer, such as carboxymethyl ethyl cellulose, hydroxypropyl methyl cellulose phthalate, methyl methacrylate-methacrylic acid copolymer, the method of conversion to a soluble salt, the method of forming a clathrate compound using cyclodextrin, etc. Moreover, 1 or a combination of 2 or more of these methods can be used, and the above-mentioned additives and these methods can be combined. It is also possible to coat the core when necessary. There are no special restrictions to the coating base used in the present invention as long as it is pharmaceutically acceptable and the purpose of the present invention can be accomplished, and a polymer base such as hydroxypropyl methyl cellulose, etc., is an example. It is also possible to use 1 or a suitable combination of 2 or more appropriate polymer bases.

The hydrogel-forming polymer substance used for the outer layer of the core here means a hydrogel-forming polymer substance with which this dry-coated tablet absorbs the water component retained in the upper digestive tract and gels and is eroded as a result of the contractile movement of the digestive tract that occurs with the digestion of food, leading to disintegration of the core tablet after a specific amount of time. Particularly ideal hydrogel-forming polymer substances have properties including viscosity during gelling to such an extent that they withstand the contractile movement of the digestive tract that accompanies the digestion of food when they are all but gelled as a result of this dry coated tablet having absorbed the water retained in the upper digestive tract and although eroded, move to the lower digestive tract retaining their shape to a certain extent and there can be disintegrated or peeled, etc. For instance, a polymer substance having a viscosity of an aqueous 1% solution (25° C.) of 1,000 cps or higher is preferred. Moreover, the properties of the polymer substance depend on its molecular weight. Consequently, polymers with a higher molecular weight are preferred as the polymer that forms a hydrogel that can be used in this dry-coated tablet. One with a viscosity-average molecular weight of 2,000,000 or higher, particularly a viscosity-average molecular weight of 4,000,000 or higher is preferred. Examples of this polymer substance are POLYOX® WSR-303 (viscosity-average molecular weight: 7,000,000, viscosity: 7,500-10,000 cP (aqueous 1% solution, 25° C.)), POLYOX® WSR Coagulant (viscosity-average molecular weight: 5,000,000, viscosity: 5,500-7,500 cP (aqueous 1% solution, 25° C.)), POLYOX® WSR-301 (viscosity-average molecular weight: 4,000,000: viscosity: 1,650-5,500 cP (aqueous 1% solution, 25° C.)), and POLYOX® WSRN-60K (viscosity-average molecular weight: 2,000,000, viscosity: 2,000-4,000 cP (aqueous 2% solution, 25° C.)) (all made by Union Carbide), ALKOX® E-75 (viscosity-average molecular weight: 2,000,000~2,500,000, viscosity: 40-70 cP (aqueous 0.5% solution, 25° C.)), ALKOX® E-100 (viscosity average molecular weight: 2,500,000~3,000,000, viscosity: 90-110 cP (aqueous 0.5% solution, 25° C.)), ALKOX® E-130 (viscosity-average molecular weight: 3,000,000~3,500,000, viscosity: 130-140 cP (aqueous 0.5% solution, 25° C.)), ALKOX® E-160 (viscosity-average molecular weight: 3,600,000~4,000,000, viscosity: 150-160 cP (aqueous 0.5% solution, 25° C.)), and ALKOX® E-240 (viscosity-average molecular weight: 4,000,000~5,000,000, viscosity: 200-240 cP (aqueous 0.5% solution, 25° C.)) (all made by Meisei Kagaku Co., Ltd.), PEO-8 (viscosity-average molecular weight: 1,700,000~2,200,000, viscosity: 20-70 cP (aqueous 0.5% solution, 25° C.)), PEO-15 (viscosity-average molecular weight: 3,300,000~3,800,000, viscosity: 130-250 cP (aqueous 0.5% solution, 25° C.), PEO-18 (viscosity-average molecular weight: 4,300,000~4,800,000, viscosity: 250-480 cp (aqueous 0.5% solution, 25° C.) (all made by Seitetsu Kagaku Co., Ltd.), etc. However, polyethylene oxide with a molecular weight of 2,000,000 or higher is particularly ideal.

The polymer substance of the present invention can be 1 or a combination of 2 or more with different molecular weights, grades, etc., in order to adjust lag time. Moreover, a mixture with another hydrogel-forming polymer substance can also be used. In addition, the core can comprise these hydrogel-forming polymer substances as long as the effects of the timed-released pharmaceutical preparation of the present invention are not lost. Sustained release of the drug after lag time is possible when the hydrogel-forming polymer substance comprises the core. The above-mentioned are also examples of the hydrogel-forming polymer substance in this case, and polyethylene oxide is preferred. Approximately 10~approximately 50 wt % of the tablet is preferred as the specific amount added.

In order for drug release to be possible in the lower digestive tract in humans, it is necessary to have a gelled outer layer at least 2 hours after administration and further, the outer layer must be disintegrated or peeled and the core released when the lower digestive tract is reached. Although it varies with the size of the pharmaceutical preparation, the type of polymer substance, the drug and hydrophilic base, content, etc., the preferred embodiment for forming an outer layer with this type of property is a pharmaceutical preparation of 600 mg or less per one tablet where the ratio of polymer substance that will form a hydrogel to the entire pharmaceutical preparation is approximately 5~approximately 95%. Approximately 10~approximately 90 wt % is further preferred. Moreover, it is preferred that the amount of hydrogel-forming polymer substance added per 1 tablet pharmaceutical preparation be approximately 20 mg or more per 1 tablet, and approximately 30 mg or more is further preferred.

Furthermore, when polyethylene oxide is used as the hydrogel-forming polymer substance, it is preferred that yellow ferric oxide and/or red ferric oxide be added as stabilizer to the outer layer of this dry-coated tablet, or that the dry-coated tablet be coated with these, so that there will be no changes in drug release performance, even if the pharmaceutical preparation is stored exposed to light. The yellow ferric oxide or red ferric oxide used in the present invention can be used alone or as a mixture.

There are no special restrictions to the mixture ratio of yellow ferric oxide and/or red ferric oxide used at this time as long as it stabilizes the dry-coated tablet without compromising the timed-release of the present invention. This mixture ratio varies with the type and method of addition, but when added to the outer layer, approximately 1~approximately 20 wt % is preferred, and approximately 3 to approximately 15 wt % is further preferred, in terms of the total amount of pharmaceutical preparation. For example, approximately 5~approximately 20 wt % is preferred, and approximately 10~approximately 15 wt % is further preferred, in terms of the entire pharmaceutical preparation with red ferric oxide. Approximately 1~approximately 20 wt % is preferred and approximately 3~approximately 10 wt % is further preferred with yellow ferric oxide. Approximately 0.3~approximately 2% is preferred, and approximately 0.5~approximately 1.5% is further preferred, in terms of tablet weight in the case of coating by film coating. Approximately 5~approximately 50% is preferred and approximately 10 to approximately 20% is further preferred as the concentration of yellow ferric oxide or red ferric oxide in the film at this time. It is preferred that the yellow ferric oxide and/or red ferric oxide be uniformly mixed in the outer layer when this ferric oxide is added to the outer layer. Mixing does not necessarily mean physical mixing. A variety of means, including for instance granulation with a filler that comprises the outer layer or coating the granulation product, etc., can be used. When coated on a dry-coated tablet, it is possible to dissolve or suspend the above-mentioned ferric oxide in a water-soluble polymer solution, such as hydroxypropyl methyl cellulose, etc., and coat the tablet with a thin film using a film coating device, such as a high coater (Freund Industry Co., Ltd.), etc. One or a combination of 2 or more of these methods can also be used.

The "hydrophilic base" comprising the outer layer of the above-mentioned dry-coated tablet is important in terms of the drug reaching the lower digestive tract, where there is little water component, together with water component and being time-released. This hydrophilic base is one that can be dissolved before the above-mentioned hydrogel-forming polymer substance gels. Specifically it is a hydrophilic base with which the amount of water needed for dissolution of 1 g of this base is 5 mL or less (20±5° C.), preferably 4 mL or less (same temperature). Examples of this hydrophilic base are water-soluble polymers, such as polyethylene glycol (for instance, Macrogol 400, Macrogol 1500, Macrogol 4000, Macrogol 6000, Macrogol 20000 (all made by Nihon Yushi)), polyvinyl pyrrolidone (for instance, PVP® K30 (made by BASF)), etc., sugar alcohols, such as D-sorbitol, xylitol, etc., saccharides, such as sucrose, maltose, lactulose, D-fructose, dextran (for instance, Dextran 40), glucose, etc., surfactants, such as polyoxyethylene-hydrogenated castor oil (for instance, Cremophor® RH40 (BASF), HCO-40, HCO-60 (Nikko Chemicals), polyoxyethylene-polyoxypropylene glycol (for instance, Pluronic® F68 (Asahi Denka Kogyo K.K.), etc.), or polyoxyethylene sorbitan fatty acid ester (for instance, Tween 80 (Kanto Kagaku Co., Ltd.), etc., salts such as sodium chloride, magnesium chloride, etc., organic acids, such as citric acid, tartaric acid, etc., amino acids, such as glycine, β-alanine, lysine hydrochloride, etc., aminosaccharides, such as meglumine, etc, and the like. Polyethylene glycol, sucrose, and lactulose are preferred and polyethylene glycol (particularly Macrogol 6000) is further preferred. Moreover, 1 or a combination of 2 or more hydrophilic bases can also be employed.

When hydrophilic base is added to the above-mentioned dry-coated tablet, the mixture ratio is preferably approximately 5~approximately 80 wt % per the entire dry-coated tablet, and further, preferably approximately 5~approximately 70 wt % per the entire dry-coated tablet.

The above-mentioned "hydrophilic base" and "readily erodible filler" can also be selected so that they are the same, but as previously mentioned, the "hydrophilic base" is one with which the amount of water necessary for dissolution of 1 g base is 5 mL or less (20±5° C.) and the "readily erodible filler" is one that shows a result of approximately 40~approximately 90% when the core tablet is analyzed by the method of determining the percentage erosion. Thus, because they are selected in accordance with their respective definition, the two are differentiated from one another based on the difference in properties in the present invention. That is, although one condition of the "readily erodible filler" is that it has excellent solubility in water, but another condition is that with respect to the correlation between timed release of the effective drug and other additives, the filler has the property of giving the dry-coated tablet a specific percentage erosion.

With respect to the mixture ratio of outer layer to core here, usually approximately 0.5~approximately 10 parts by weight is preferred, approximately 1~approximately 5 parts by weight is further preferred, per 1 part by weight core. Moreover, with respect to the mixture ratio of hydrophilic base and hydrogel-forming polymer substance of the outer layer, usually approximately 0.1 to approximately 8 parts by weight is preferred, approximately 0.3-approximately 5 parts by weight is further preferred, per 1 part by weight hydrogel-forming polymer substance.

BRIEF DESCRIPTION OF THE DRAWINGS

FIG. 1 is a schematic diagram showing an embodiment of the pharmaceutical composition of the present invention. FIG. (1-1) is a schematic diagram showing the preparation form (for instance, granules, powders, capsules in which these have been filled, liquid, suspension, emulsion, capsules in which liquid, suspension, emulsion, etc., has been filled, etc.) where a layer in which aminoalkyl methacrylate copolymer E (B in the figure) and acidic substance (C in the figure) have been uniformly mixed is coated on a core comprising drug (A in the figure). FIG. (1-2a) and FIG. (1-2b) are schematic diagrams showing the same composition, which is an embodiment of the invention of the present application. In the micro view, it is a composition where each component of drug (A in the figure), aminoalkyl methacrylate copolymer E (B in the figure), and acidic substance (C in the figure) does not appear to be uniformly dispersed, as shown in FIG. (1-2a), but the macro view is the composition of an embodiment of the invention of the present application where each component is present uniformly dispersed as a whole, as shown in FIG. (1-2b). The preparation form in this state is, for instance, powders, particles, capsules filled with these or their granulation product or mixture, tablets obtained by compression molding of these, and capsules filled with liquids, suspension, emulsion, etc., and the like.

PREFERRED EMBODIMENTS OF THE INVENTION

Figure 1:
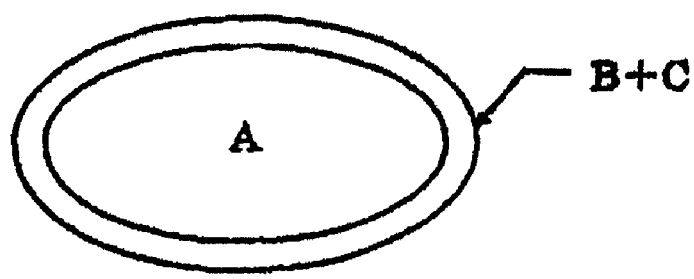
Figure 1:
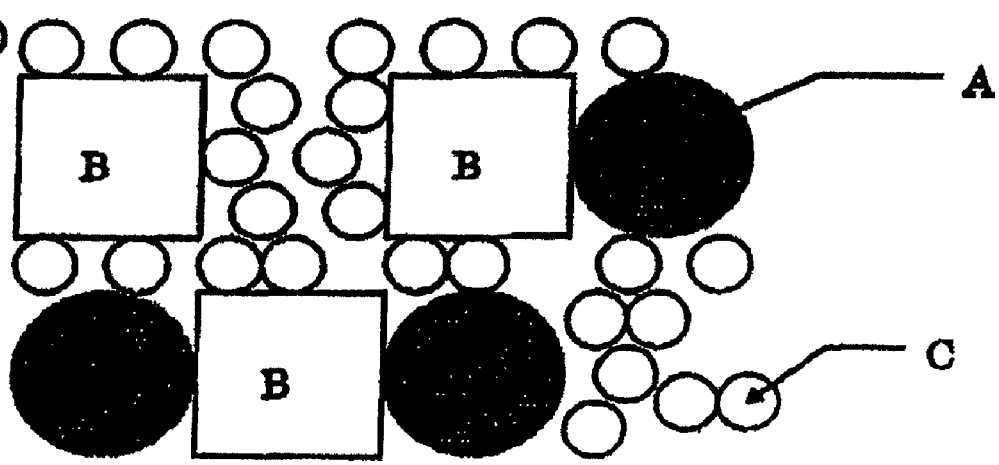
Figure 1:
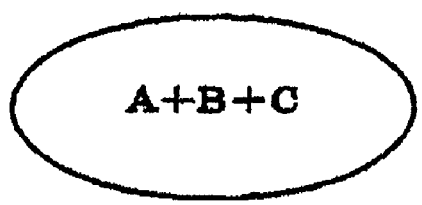

The present invention will now be described with examples, but it is not limited to these examples.

Whether or not a drug is difficult to absorb from the digestive tract due to interaction with the digestive tract mucous components can be confirmed by, for instance, the following method:

EXPERIMENT 1

COMPARATIVE EXAMPLE 1

Interaction Between Drug and Digestive Tract Mucous Layer Components

<Experimental Method> Tetracycline (TC hereafter) was dissolved in PBS buffer to a drug concentration of 0.5 mg/ml. Moreover, a PBS buffer containing 0.8% (w/v) pork stomach mucin, 6.2% (w/v) bovine serum albumin, 4.92% (w/v) linoleic acid, 0.72% (w/v) cholesterol, 0.36% (w/v) phosphatidyl choline, 1.5% (w/v) Tween 80, and 0.04% (w/v) sodium azide was prepared in accordance with the method of Angeta et al. (Angeta W. L. et al., Pharm. Res., 15, 66-71, 1998), and this liquid was used as the artificial mucous liquid. An equilibrium dialysis cell consisting of two phases was used in the experiments. A dialysis membrane with a fraction molecular weight of 50,000 (Spectra/Por®, SPECTRUM Lab., Inc.) was inserted between the 2 phases. One of the two phases served as the Donor phase (D phase hereafter) and one served as the Reservoir phase (R phase hereafter). Two milliliters TC solution were introduced to the D phase and 2 ml artificial mucous liquid were introduced to the R phase and incubation was performed in a thermostatic cell (37° C., 150 strokes/minute). The TC solution of the D phase was sampled and the drug concentration was determined every hour for up to 5 hours. The drug was determined by UV quantitative determination in accordance with the method of Braybrooks (M. P. Braybrooks, J. Pharm. Pharmacol., 27, pp. 508-515, 1975).

<Evaluation Method> The initial drug concentration of the D phase is $C_o$ and the drug concentration at equilibrium (t=∞) is $C_\infty$. Formula (I) shows a as the ratio of drug present in the R phase at t=∞ that has not bound with artificial mucous component.

$$a = C_\infty / C_o - C_\infty \tag{I}$$

When all of the drug that has moved to the R phase has been adsorbed on the artificial mucous components, a=0, and when none has adsorbed, a=1. Therefore, a was used as a parameter that indicates adsorptivity of drugs on artificial mucous components.

$C_\infty$: calculated by deriving the drug concentration-time formula and substituting t=∞.

$C_o$: drug concentration when experiment started (0.5 mg/ml)

Reference 1

An experiment was performed and a was calculated by the same method as entered under Experiment 1 using artificial mucous obtained by mixing 0.5 mg/ml TC solution to the D phase of the equilibrium dialysis cell and 3% Eudragit™ EPO (Röhm GmRH) to the R phase.

EXAMPLE 1

1,650 g Eudragit™ E100 (Röhm GmRH) and Tween 80 at a ratio of 10:1 were dissolved in 12,000 g 1 mol/l aqueous hydrochloric acid.ethanol mixture (5:12) to obtain the spraying liquid. The spraying liquid was spray dried at a spraying speed of 30 g/minute, intake temperature of 85° C., and exhaust temperature of 62-66° C. using the model L-8 Spray Dryer (Ohkawara Seisakujo). After drying for 24 hours at 40° C., a white powder was obtained (E-SD hereafter; used in the following Examples, Experiments, Comparative Examples, etc., unless otherwise specified). An experiment was performed and a was calculated by the same method as in Experiment 1 using artificial mucous obtained by dissolving 0.5 mg/ml TC solution in the D phase of the equilibrium dialysis cell and 3% E-SD in the R phase.

Control 1

An experiment was performed and a was calculated by the same method as in Experiment 1 using 0.5 mg/ml TC solution in the D phase of the equilibrium dialysis cell and PBS buffer in the R phase.

<Evaluation>

With the a value obtained in Control 1 serving as 100, the a value of Comparative Example 1 (Experiment 1) and Example 1 to this value (%) is shown in Table 1.

TABLE 1

| | Control 1 | Comparative Example 1 | Reference 1 | Example 1 |
|---|---|---|---|---|
| a (% of Control) | 100 | 48.8 | 74.3 | 71.9 |

<Results and Discussion>

The a value of Comparative Example 1 (Experiment 1) was approximately 50% that of Control 1, indicating that the TC was firmly bound to the artificial mucous components. In contrast to this, according to the results of Example 1, the a value was improved to approximately 70% that of Control 1 by mixing aminoalkyl methacrylate copolymer E and acidic substance in the artificial mucous. Consequently, this indicates that a composition in which aminoalkyl methacrylate copolymer E and an acidic substance, for instance, hydrochloric acid, etc., have been uniformly mixed has the effect of increasing the ratio of drug that is not bound to mucus by co-existing with mucous components. Furthermore, the results of Reference Example 1 revealed that in vitro there was an improvement in the a value to at least approximately 70% that of Control 1, but this result could not be confirmed in vivo.

EXPERIMENT 2

Control 2

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Eighty mg TC were weighed out and dissolved in 100 ml PBS buffer to obtain an aqueous 0.8 mg/ml TC solution (hereafter referred to as solution A). Ten milliliters solution A and 10 ml PBS buffer were mixed with a vortex mixer and mixture in an amount corresponding to 10 mg/kg TC was administered through the intestinal loop. Blood was drawn from the jugular vein 0, 0.25, 0.5 and 1 hour after administration and the plasma concentration of unaltered form (μg/ml) was determined by high-performance liquid chromatography in accordance with the Nilsson-Ehle method (I. Nilsson-Ehle, Acta Path. microbiol. scand. Sect. B, Suppl. 259: pp. 61-66 (1977)). The maximum plasma concentration (Cmax) and area under concentration curve (AUC) were calculated from the changes in the plasma concentration that were obtained.

EXAMPLE 2

Six grams E-SD were weighed out and dissolved in 100 ml PBS buffer solution to obtain an aqueous 60 mg/ml solution (solution B hereafter). Ten milliliters solution A and 10 ml solution B were mixed with a vortex mixer. The solution was administered through the rat intestinal loop and the plasma concentration of unaltered form was determined by the same method as in Experiment 2. The Cmax and AUC were calculated from the changes in the plasma concentration that were obtained.

EXAMPLE 3

Eudragit™ EPO (Röhm GmRH) was dissolved in aqueous hydrochloric acid and lyophilized (the lyophilized product is E-FD hereafter). Six g E-FD were weighed out and dissolved in 100 ml PBS buffer solution to obtain an aqueous 60 mg/ml solution (solution C hereafter). Ten milliliters solution A and 10 ml solution C were mixed with a vortex mixer. The solution was administered through the rat intestinal loop and the plasma concentration of unaltered form was determined by the same method as in Experiment 2. The Cmax and AUC were calculated from the changes in the plasma concentration that were obtained.

COMPARATIVE EXAMPLE 2

(Confirmation of Improvement of Absorption by Enteric Polymer Base)

Eudragit™ L100 (Röhm GmRH) was dissolved in aqueous sodium hydroxide solution and lyophilized (the lyophilized product is L-FD hereafter). Six g L-FD were weighed out and dissolved in 100 ml PBS buffer solution to obtain an aqueous 60 mg/ml solution (solution D hereafter). Ten milliliters solution A and 10 ml solution D were mixed with a vortex mixer. The solution was administered through the rat intestinal loop and the plasma concentration of unaltered form was determined by the same method as in Experiment 2. The Cmax and AUC were calculated from the changes in the plasma concentration that were obtained. The Cmax and AUC that were found in Experiment 2, Comparative Example 2, Example 2 and Example 3 are shown in Table 2.

TABLE 2

|  | Cmax (µg/ml) | AUC (µg · min/ml) |
| --- | --- | --- |
| Control 2 | 0.79 ± 0.31 | 22.05 ± 2.84 |
| Example 2 | 3.47 ± 0.01 | 158.80 ± 1.80 |
| Example 3 | 3.64 ± 0.32 | 174.53 ± 13.78 |
| Comparative Example 2 | 0.63 ± 0.07 | 16.79 ± 3.26 |

<Results and Discussion>

There was a marked increase in Cmax and AUC in Example 2 and Example 3 when compared to Experiment 2. In Example 2, the Cmax was approximately 4-times that of Experiment 2 and the AUC was approximately 7-times that of Experiment 2. In Example 3, Cmax was approximately 4.5-times that of Experiment 2 and AUC was approximately 8-times that of Example 2. Based on these results, it is clear that the plasma concentration of TC is increased by using aminoalkyl methacrylate copolymer E and acidic substance.

On the other hand, Cmax and AUC of Comparative Example 2 in which Eudragit™ L100, which is an enteric polymer, was used were not different from those of Experiment 2. Consequently, it became clear that a composition in which aminoalkyl methacrylate copolymer E and acidic substance, such as hydrochloric acid, etc., have been uniformly mixed has the effect of promoting absorption of TC from the digestive tract in vivo.

COMPARATIVE EXAMPLE 3

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. 80 mg TC were weighed out and dissolved in 100 ml PBS buffer to obtain an aqueous 0.8 mg/ml TC solution (solution A hereafter). Six grams Eudragit™ EPO (Röhm GmRH) were weighed out and dispersed in 100 ml PBS buffer to obtain a 60 mg/ml dispersion (solution E hereafter). Ten milliliters solution A and 10 ml solution E were mixed with a vortex mixer. This mixture was circulated through the rat intestinal loop and the plasma concentration of unaltered form was determined by the same method as in Experiment 2. The maximum plasma concentration (Cmax) and area under concentration curve (AUC) were calculated from the changes in the plasma concentration that were obtained. The Cmax and AUC found in Experiment 2, Example 3 and Comparative Example 3 are shown in Table 3.

TABLE 3

|  | Cmax (µg/ml) | AUC (µg · min/ml) |
| --- | --- | --- |
| Control 2 | 0.79 ± 0.31 | 22.05 ± 2.84 |
| Example 3 | 3.47 ± 0.01 | 158.80 ± 1.80 |
| Comparative Example 3 | 0.64 ± 0.24 | 11.80 ± 4.88 |

(Mean value ± S.D., n = 3)

<Results and Discussion>

As with E-SD, Eudragit™ EPO prevented binding of TC with artificial mucus in experiments using in vitro equilibrium dialysis, but the effect of promoting absorption of TC was not seen in vivo. The reason for this is apparently that although EPO was dissolved in the linoleic acid contained in the artificial mucus so that interaction was inhibited in vitro, in vivo there was not sufficient acidic oil, such as linoleic acid, etc., to dissolve the EPO that had been administered and therefore, absorption of the TC was not improved. Consequently, it appears that absorption of a drug can be improved using Eudragit™ E by uniformly mixing the Eudragit™ E and acidic substance. Moreover, when a drug and Eudragit™ E are orally administered, there is a chance that digestive tract absorption of the drug will not be improved in humans with achlorhydria because the Eudragit™ E will not be dissolved in the small intestine of course, or in the stomach. Consequently, it appears that by unifommly mixing Eudragit™ E and acidic substance, it is possible to improve with more certainty drug absorption using Eudragit™ E.

EXPERIMENT 3

Control 3

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Twenty milligrams TC and 500 mg lactose were weighed out and thoroughly mixed with a mortar and pestle. Fifty-two milligrams of the mixed powder that was obtained were molded into tablet form and administered through the rat intestinal loop using a plastic tube. Blood was drawn from the jugular vein 0, 0.25, 0.5 and 1 hour after administration and the plasma concentration of unaltered form (µg/ml) was determined by high-performance liquid chromatography by the same method as in Experiment 2. Cmax and AUC were calculated from the changes in the plasma concentration that were obtained.

EXAMPLE 4

Twenty milligrams TC and 500 mg E-SD were weighed out and thoroughly mixed with a mortar and pestle. Fifty-two milligrams of the mixed powder that was obtained was molded into tablet form. The tablet was circulated through the rat intestinal loop and the plasma concentration of unaltered form was determined by the same method as in Experiment 3. Cmax and AUC were calculated from the changes in the plasma concentration that were obtained. Cmax and AUC that were found in Experiment 3 and Example 4 are shown in Table 4.

TABLE 4

|  | Cmax (µg/ml) | AUC (µg · min/ml) |
|---|---|---|
| Test 3 | 0.36 ± 0.06 | 5.37 ± 0.88 |
| Example 4 | 1.05 ± 0.38 | 30.41 ± 2.85 |

(Mean value ± S.D.)

<Results and Discussion>

An increase in the plasma concentration of the drug was seen in Example 4 when compared to Experiment 3. Cmax was approximately 3-times that of Experiment 3 and AUC was approximately 6-times that of Experiment 3 in Example 4. Consequently, it became clear that aminoalkyl methacrylate copolymer E has the effect of promoting absorption of a drug by being dissolved in the digestive tract, whether it is administered in solution form or solid form.

Compound B in Experiment 4, Experiment 5, and Example 5, etc., below is [1-hydroxy-2-imidazo-(1,2-a)pyridin-3-yl-ethylidene]bis-phosphonate), which was made by the method in Japanese Kokoku Patent No. Hei 6-99457.

EXPERIMENT 4

COMPARATIVE EXAMPLE 4

Five milliliters of an aqueous 0.5 mg/ml compound B solution were prepared and 5 ml distilled water were added to this and thoroughly mixed to obtain the prepared liquid. Another 2 ml distilled water were added to this liquid to obtain control liquid A. The number of insoluble particulate matter (10 µm or larger) in control liquid A was determined 0, 15, 30 and 60 minutes after preparation using an insoluble particulate matter gauge (brand name HIAC/ROYCO®, Pacific Scientific).

EXPERIMENT 5

COMPARATIVE EXAMPLE 5

Five milliliters of an aqueous 0.5 mg/ml compound B solution were prepared and 5 ml distilled water were added to this and thoroughly mixed to obtain the prepared liquid. Two milliliters of aqueous 10 mg/ml calcium chloride.2H$_2$O solution were added to this liquid to obtain control liquid B. The number of insoluble particulate matter (10 µm or larger) in control liquid B was determined 0, 15, 30 and 60 minutes after preparation by the same method as in Experiment 4.

EXAMPLE 5

Five milliliters each of aqueous 0.05% E-SD solution, aqueous 0.1% E-SD solution, aqueous 1.0% E-SD solution, and aqueous 2.0% E-SD solution were added to 5 ml of aqueous 0.5 mg/ml compound B solution and thoroughly mixed to obtain aqueous compound B solutions comprising 0.025%, 0.05%, 0.5% and 1.0% E-SD. Two milliliters aqueous 10 mg/ml calcium chloride solution were added to each of these prepared solutions and the number of insoluble particulate matter (10 µm or larger) was determined 0, 15, 30 and 60 minutes after addition by the same method as in Experiment 4.

<Results and Discussion>

Figure 2:
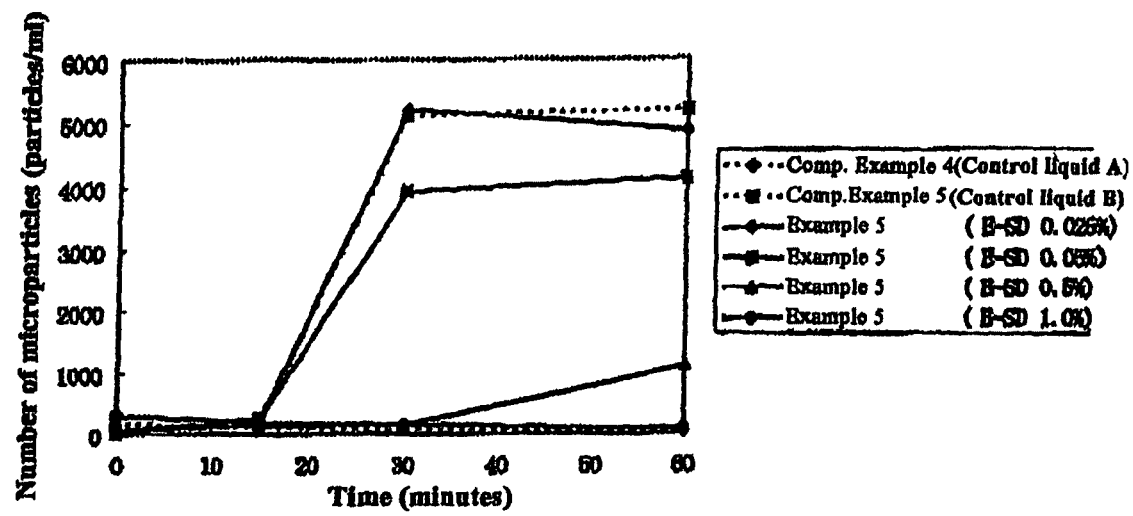
FIG. 2 is a diagram showing changes over time in the number of insoluble particulate matter determined in Comparative Example 4, Comparative Example 5, and Example 5.

FIG. 2 shows changes over time in the number of insoluble particulate matter determined in Comparative Example 4, Comparative Example 5, and Example 5. Based on the results in Comparative Examples 4 and 5, an increase in the number of insoluble particulate matter was seen when aqueous calcium chloride solution was added to the aqueous compound B solution. In contrast to this, the formation of insoluble particulate matter was inhibited dependent on the E-SD concentration in Example 5 when the E-SD was dissolved, that is, when aqueous calcium chloride solution was added to the aqueous compound B solution comprising aminoalkyl methacrylate copolymer E and hydrochloric acid. Results were seen from a low concentration of at least 0.05%. Consequently, it is confirmed that aminoalkyl methacrylate copolymer E in the presence of acidic substance has the effect of inhibiting the formation of an insoluble complex between drug and metal ions.

EXPERIMENT 6

COMPARATIVE EXAMPLE 6

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Eighty milligrams compound B were weighed out and dissolved in 100 ml PBS buffer to obtain an aqueous 0.8 mg/ml TC solution (solution A hereafter). Ten milliliters solution A and 10 ml PBS were mixed with a vortex mixer. This mixed solution was administered through the rat intestinal loop in an amount corresponding to 10 mg/kg compound B. Blood was drawn from the jugular vein 0, 0.25, 0.5 and 1 hour after administration and the plasma concentration of unaltered form (ng/ml) was determined by the fluorescence detection method using high-performance liquid chromatography in accordance with the method of Usui et al. (T. Usui et al., J. Chromatogr. B 652 (1994)).

EXAMPLE 6

Four grams E-SD were weighed out and dissolved in 100 ml PBS buffer solution to obtain an aqueous 40 mg/ml solution (solution B hereafter). Ten milliliters solution A and 10 ml solution B were mixed with a vortex mixer. The mixed was administered through the rat intestinal loop solution in an amount corresponding to 10 mg/kg compound B and the plasma concentration of unaltered form was determined by the same method as in Comparative Example 6.

<Results and Discussion>

Figure 3:
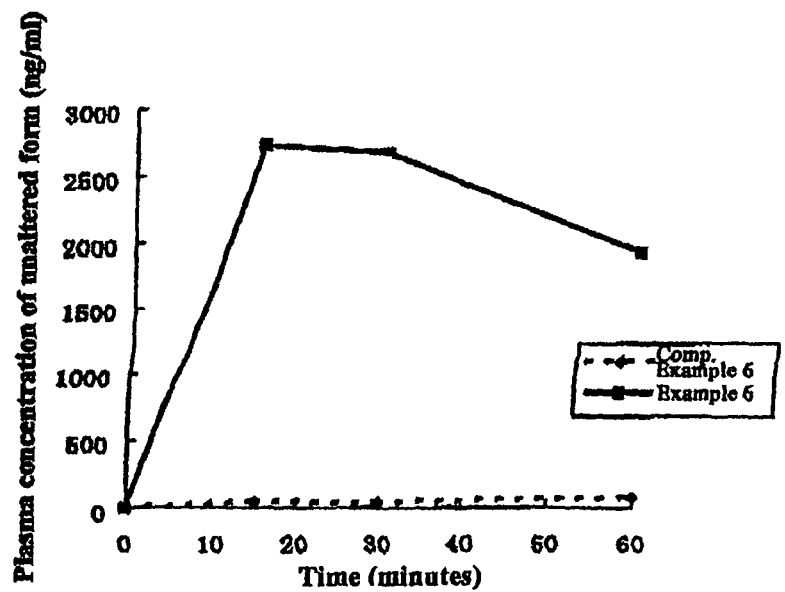
FIG. 3 is a diagram showing changes in the plasma concentration of unaltered form found in Comparative Example 6 and Example 6.

FIG. 3 shows the changes in the plasma concentration of unaltered form found in Comparative Example 6 and Example 6. These results indicate that aminoalkyl methacrylate copolymer E improves oral absorption of compound B, which forms a slightly soluble complex with the calcium ions that are present in the digestive tract mucous membrane and/or mucous layer.

EXPERIMENT 7

Control 4

Ten milligrams compound B and 190 mg lactose were mixed and tablets were prepared by tableting under a tableting pressure of 40 kg/cm$^2$ using an oil press. The tablets for the control were orally administered together with 30 ml water to beagles (15-24 months old) under fasting conditions. Approximately 3 ml blood were drawn from the brachial veins of the front limbs over time up to 8 h after administration and the plasma concentration of unaltered form (ng/ml) was determined by the same method as in Comparative Example 6. The maximum plasma concentration (Cmax) and area under concentration curve (AUC) were calculated from the changes in the plasma concentration that were obtained.

EXAMPLE 7

Ten milligrams compound B, 125 mg E-SD, and 65 mg lactose were mixed and tablets were prepared by tableting under a tableting pressure of 40 kg/cm$^2$ using an oil press. These tablets were orally administered to beagles, blood was drawn and the plasma concentration of unaltered form was determined under the same conditions as in Experiment 7. Cmax and AUC were determined from changes in the plasma concentration that were obtained. Cmax and AUC that were found in Control 4 and Example 7 are shown in Table 5.

TABLE 5

|  | Cmax (ng/ml) | AUC 0.8 h (ng · h/ml) |
| --- | --- | --- |
| Control 4 | 7.7 ± 3.9 | 18.9 ± 7.1 |
| Example 7 | 56.6 ± 26.0 | 108.1 ± 64.0 |

(Mean value ± S.D., n = 6)

<Results and Discussion>

Cmax and AUC of Example 7 were approximately 7.4-times and approximately 5.7-times those of Control 4, respectively, with there being a marked increase in Cmax and AUC when compared to Control 4.

It became clear from this finding that aminoalkyl methacrylate copolymer E has the effect of promoting absorption of compound B from the digestive tract.

EXAMPLE 8

Enteric Tablets

Tablets coated with 1.2% HPMC were obtained by spraying (spraying conditions: number of revolutions 12 rpm, intake temperature 56-60° C., exhaust temperature 44-46° C., spraying speed 4-10 g/min) the tablets obtained in Example 7 with an aqueous 10% HPMC (brand name TC-5E, Shin-etsu Chemical Co., Ltd.) solution using Hicoater (brand name HCT-30 Hicoater, Freund). Enteric coated tablets were prepared by coating with 2.7% enteric coating base by spraying (spraying conditions: number of revolutions 12 rpm, intake temperature 52° C., exhaust temperature 40° C., spraying speed 4-8 g/min) a solution of 10% (enteric base (Eudragit L: Triethyl citrate=9:1) in a water/ethanol (1:17) mixture using a Hicoater. These tablets were orally administered to beagles, blood was drawn, and the plasma concentration of unaltered form was determined under the same conditions as in Experiment 7. Cmax and AUC were calculated from the changes in the plasma concentration that were obtained.

EXAMPLE 9

Sustained-Release Tablets

Tablets were prepared by mixing 10 mg compound B, 125 mg E-SD, 20 mg polyethylene oxide (brand name Polyox WSR303, Union Carbide), and 45 mg Macrogol 6000 and tableting under a tableting pressure of 40 kg/cm$^2$ using an oil press. These tablets were orally administered to beagles, blood was drawn, and the plasma concentration of unaltered form was determined under the same conditions as in Experiment 7. Cmax and AUC were calculated from the changes in the plasma concentration that were obtained.

EXAMPLE 10

Timed-Release Tablets

Tablets were prepared to obtain core tablets by mixing 10 mg compound B, 125 mg E-SD, and 65 mg sucrose and tableting under a tableting pressure of 40 kg/cm$^2$ using an oil press. Fifty milligrams polyethylene oxide (brand name Polyoxy WSR303) and 250 mg Macrogol 6000 were mixed to prepare polyethylene oxide/Macrogol 6000. Half was added to a tableting mortar and then the core was placed in the center of the mortar. Next, half of the remainder of the above-mentioned mixed powder was added to the mortar and tablets with an outer layer were prepared by tableting under a tableting pressure of 40 kg/cm$^2$ using an oil press. These dry-coated tablets were orally administered to beagles, blood was drawn and the plasma concentration of unaltered form was determined under the same conditions as in Experiment 7. Cmax and AUC were calculated from the changes in the plasma concentration that were obtained. Cmax and AUC that were found in Control 4, Example 8, Example 9, and Example 10 are shown in Table 6.

TABLE 6

|  | Cmax (ng/ml) | AUC 0.8 h (ng · h/ml) |
| --- | --- | --- |
| Control 4 | 7.7 ± 3.9 | 18.9 ± 7.1 |
| Example 8 | 14.0 ± 13.0 | 39.7 ± 25.4 |
| Example 9 | 35.3 ± 25.3 | 102.2 ± 88.2 |
| Example 10 | 20.0 ± 9.6 | 63.9 ± 32.9 |

(Mean value ± S.D., n = 3-6)

<Results and Discussion>

Example 8, Example 9, and Example 10 showed a marked increase in the Cmax and AUC when compared to Control 4. It became clear from these results that absorption of compound B from the digestive tract is promoted with pharmaceutical preparations in which aminoalkyl methacrylate copolymer E and acidic substance have been uniformly mixed in a variety of preparation types, including enteric pharmaceutical preparations, sustained-release pharmaceutical preparations, timed-release pharmaceutical preparations, etc.

Compound C below is incadronate [(cycloheptylamino)-methylene]bis-phosphonate made by the method in Japanese Patent No. Hei 7-629.

EXPERIMENT 8

COMPARATIVE EXAMPLE 7

Five milliliters of aqueous 0.5 mg/ml compound C solution were prepared. Five milliliters distilled water and 2 ml of an aqueous 15.12 mg/ml sodium bicarbonate solution were added to this and thoroughly mixed to obtain a prepared liquid. Another 2 ml distilled water were added to this liquid. The number of insoluble particulate matter (10 μm or larger) was determined 0, 15, 30 and 60 minutes after addition using an insoluble particulate matter gauge (brand name HIAC/ROYCO®, Pacific Scientific).

COMPARATIVE EXAMPLE 8

Five milliliters of an aqueous 0.5 mg/ml compound C solution were prepared. Five milliliters distilled water and 2 ml of an aqueous 15.12 mg/ml sodium bicarbonate solution were added to this and thoroughly mixed to obtain a prepared liquid. Two milliliters of an aqueous 10 mg/ml calcium chloride.$2H_2O$ solution were added to this liquid and the number of insoluble particulate matter (10 μm or larger) were determined 0, 15, 30, and 60 minutes after addition by the same method as in Experiment 8.

EXAMPLE 11

Figure 4:
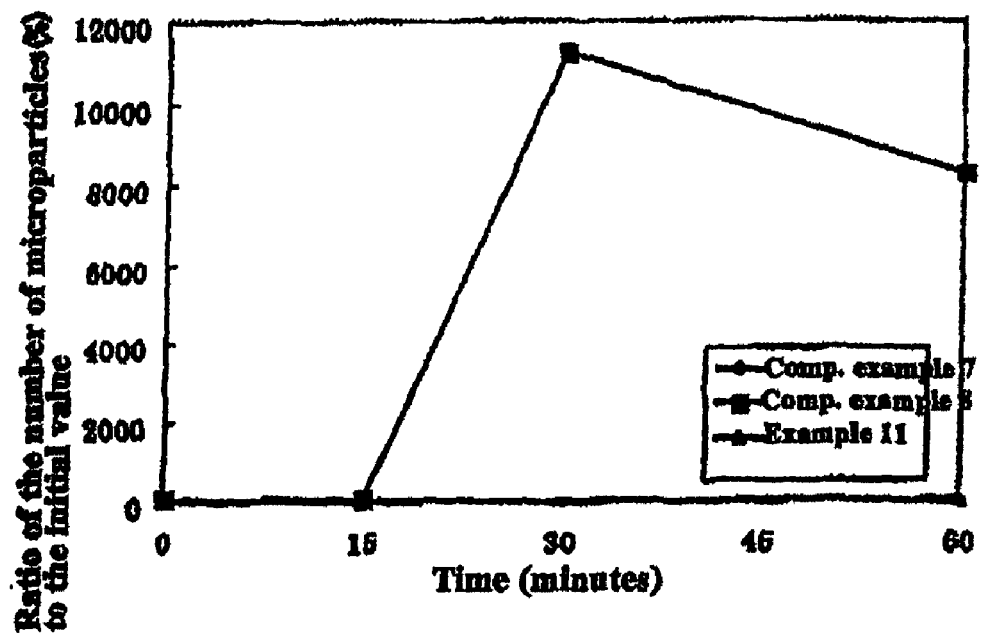
FIG. 4 is a diagram showing changes over time in the number of insoluble particulate matter determined in Comparative Example 7, Comparative Example 8, and Example 11.

Five milliliters of an aqueous 0.5 mg/ml compound C solution were prepared. Five milliliters of an aqueous 30 mg/ml E-SD solution and 2 ml of an aqueous 15.12 mg/ml sodium bicarbonate solution were added to this and thoroughly mixed to obtain a prepared solution. Then 2 ml of an aqueous 10 mg/ml calcium chloride.$2H_2O$ solution were added to this liquid. The number of insoluble particulate matter (10 μm or larger) was determined 0, 15, 30 and 60 minutes after addition by the same method as in Example 8. Changes over time in the number of insoluble particulate matter determined in above-mentioned Comparative Example 7, Comparative Example 8, and Example 11 are shown in FIG. 4.

<Results and Discussion>

According to the results of Comparative Example 7 and Comparative Example 8, an increase in the number of insoluble particulate matter was seen when aqueous calcium chloride solution was added to aqueous compound C solution. The formation of insoluble particulate matter was inhibited when aqueous calcium chloride solution was added to aqueous compound C solution in which E-SD had been dissolved in Example 11. This confirms that aminoalkyl methacrylate copolymer E has the effect of inhibiting the formation of a slightly soluble complex between compound C and metal (calcium) ions.

Compound D (etidronate) below is (1-hydroxyethylidene)-1,1-bisphosphonate.

EXPERIMENT 9

COMPARATIVE EXAMPLE 9

Five milliliters of aqueous 0.5 mg/ml compound D solution were prepared and 5 ml distilled water and 0.1 ml aqueous 15.12 mg/ml sodium bicarbonate solution were added to this and thoroughly mixed to obtain the prepared liquid. Another 2 ml distilled water were added to this liquid, and the number of insoluble particulate matter (2 μm or larger) was determined 0, 15, 30 and 60 minutes after addition using an insoluble particulate matter gauge (brand name HIAC/ROYCO®, Pacific Scientific).

COMPARATIVE EXAMPLE 10

Five milliliters aqueous 0.5 mg/ml compound D solution were prepared and 5 ml distilled water and 0.1 ml aqueous 15.12 mg/ml sodium bicarbonate solution were added to this, and thoroughly mixed to obtain the prepared liquid. Two milliliters aqueous 10 mg/ml calcium chloride.$2H_2O$ solution were added to this, and the number of insoluble particulate matter (2 μm or larger) was determined 0, 15, 30 and 60 minutes after addition by the same method as in Experiment 9.

EXAMPLE 12

Figure 5:
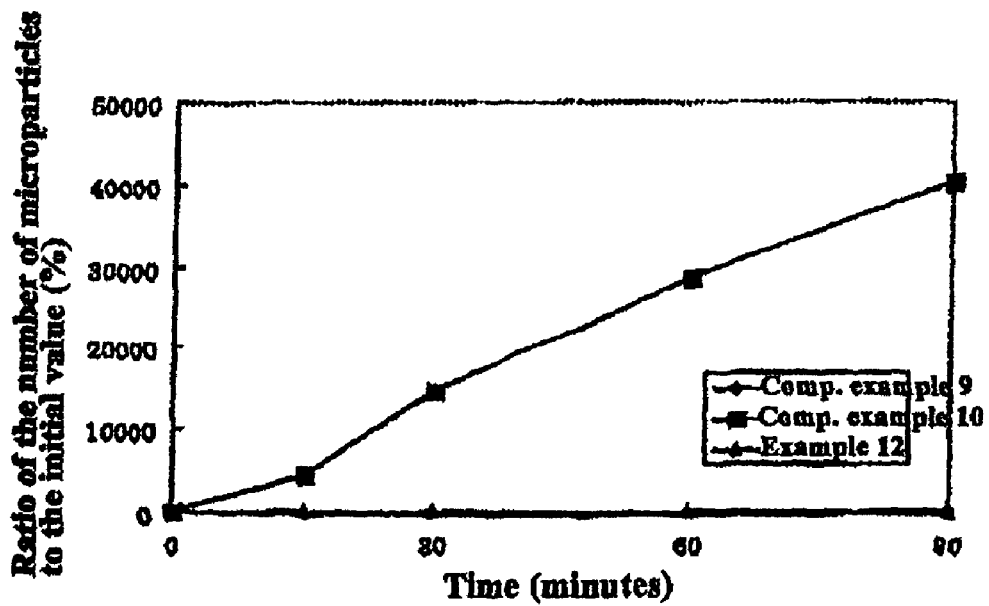
FIG. 5 is a diagram showing changes over time in the number of insoluble particulate matter determined in Comparative Example 9, Comparative Example 10, and Example 12.

Five milliliters aqueous 0.5 mg/ml compound D solution were prepared and then 5 ml aqueous 30 mg/ml E-SD solution and 0.1 ml aqueous 15.12 mg/ml sodium bicarbonate solution were added to this and thoroughly mixed to obtain the prepared liquid. Two milliliters aqueous 10 mg/ml calcium chloride.$2H_2O$ solution were added to this and the number of insoluble particulate matter (2 μm or larger) was determined 0, 15, 30, and 60 minutes after addition by the same method as in Experiment 9. Changes over time in the number of insoluble particulate matter determined in above-mentioned Comparative Example 9, Comparative Example 10, and Example 12 are shown in FIG. 5.

<Results and Discussion>

According to the results in Comparative Example 9 and Comparative Example 10, there was an increase in the number of insoluble particulate matter when aqueous calcium chloride solution was added to aqueous compound D solution. Formation of insoluble particulate matter was inhibited when aqueous calcium chloride solution was added to aqueous compound D solution in which E-SD had been dissolved in Example 12. This confirms that aminoalkyl methacrylate copolymer E has the effect of inhibiting the formation of a slightly soluble complex between compound D and metal (calcium) ions.

Compound E (alendronate) below is 4-amino-1-hydroxy butylidene 1,1-bisphosphonate.

EXPERIMENT 10

COMPARATIVE EXAMPLE 11

Five milliliters of an aqueous 0.5 mg/ml compound E solution were prepared and 5 ml distilled water and 3 ml aqueous 15.12 mg/ml sodium bicarbonate solution were added to this and thoroughly mixed to obtain a prepared liquid. Another 2 ml distilled water were added to this liquid, and the number of insoluble particulate matter (2 μm or larger) was determined 0, 15, 30, and 60 minutes after addition using an insoluble particulate matter gauge (brand name HIAC/ROYCO®, Pacific Scientific).

COMPARATIVE EXAMPLE 12

Five milliliters aqueous 0.5 mg/ml compound E solution were prepared and 5 ml distilled water and 3 ml aqueous 15.12 mg/ml sodium bicarbonate solution were added to this and thoroughly mixed to obtain the prepared liquid. Two milliliters aqueous 10 mg/ml calcium chloride.2H$_2$O solution were added to this liquid, and the number of insoluble particulate matter (2 µm or larger) was determined 0, 15, 30 and 60 minutes after addition by the same method as in Experiment 10.

EXAMPLE 13

Figure 6:
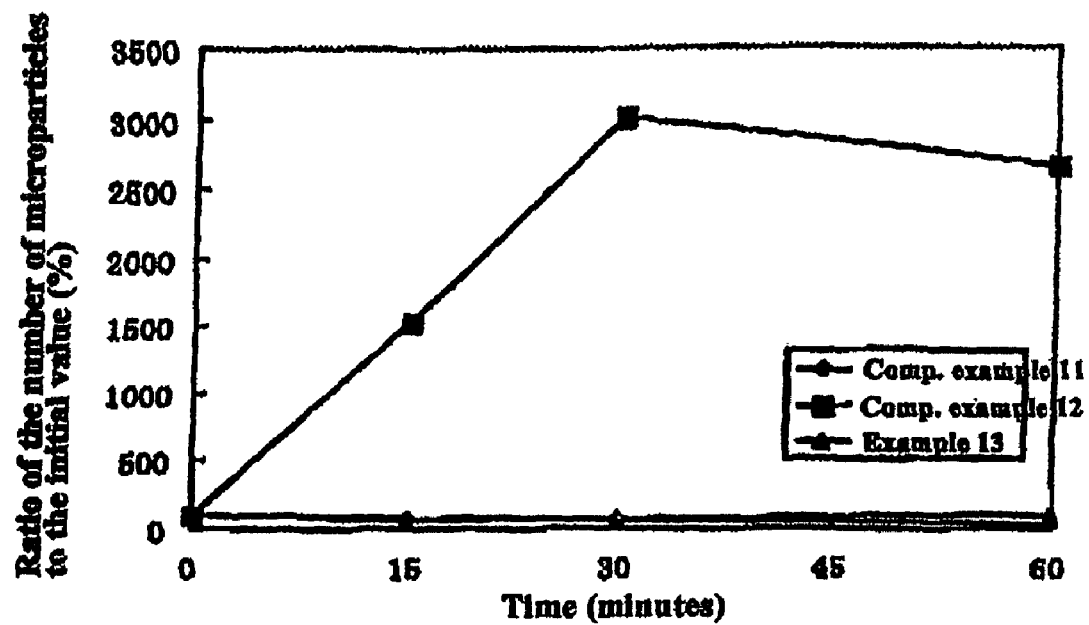
FIG. 6 is a diagram showing changes over time in the number of insoluble particulate matter determined in Comparative Example 11, Comparative Example 12, and Example 13.

Five milliliters aqueous 0.5 mg/ml compound E solution were prepared and 5 ml aqueous 30 mg/ml aqueous E-SD solution and 3 ml aqueous 15.12 mg/ml sodium bicarbonate solution were added to this and thoroughly mixed to obtain the prepared liquid. Two milliliters aqueous 10 mg/ml calcium chloride.2H$_2$O solution were added to this liquid, and the number of insoluble particulate matter (2 µm or larger) was determined 0, 15, 30, and 60 minutes after addition as in Experiment 10. The changes over time in the number of insoluble particulate matter determined in above-mentioned Comparative Example 11, Comparative Example 12, and Example 13 are shown in FIG. 6.

<Results and Discussion>

According to the results in Comparative Example 11 and Comparative Example 12, there was an increase in the number of insoluble particulate matter when aqueous calcium chloride solution was added to aqueous compound E solution. The formation of insoluble particulate matter was inhibited when aqueous calcium chloride solution was added to aqueous compound E solution in which E-SD had been dissolved in Example 13. This confirms that aminoalkyl methacrylate copolymer E has the effect of inhibiting the formation of a slightly soluble complex between compound E and metal (calcium) ions.

EXPERIMENT 11

COMPARATIVE EXAMPLE 13

Experiment Using Another Metal Ion, Magnesium

Five milliliters aqueous 0.5 mg/ml compound B solution were prepared and 5 ml distilled water and 0.1 ml aqueous 15.12 mg/ml sodium bicarbonate solution were added and thoroughly mixed to obtain the prepared liquid. Another 2 ml distilled water were added to this solution and the number of insoluble particulate matter (2 µm or larger) was determined 0, 15, 30, and 60 minutes after addition using an insoluble particulate matter gauge (HIAC/ROYCO®, Pacific Scientific).

COMPARATIVE EXAMPLE 14

Five milliliters aqueous 0.5 mg/ml compound B solution were prepared and 5 ml distilled water and 0.1 ml aqueous 15.12 mg/ml sodium bicarbonate solution were added to this and thoroughly mixed to obtain the prepared liquid. Two milliliters aqueous 10 mg/ml magnesium chloride.6H$_2$O solution were added to this prepared liquid, and the number of insoluble particulate matter (2 µm or larger) was determined 0, 15, 30 and 60 minutes after addition by the same method as in Experiment 11.

EXAMPLE 14

Figure 7:
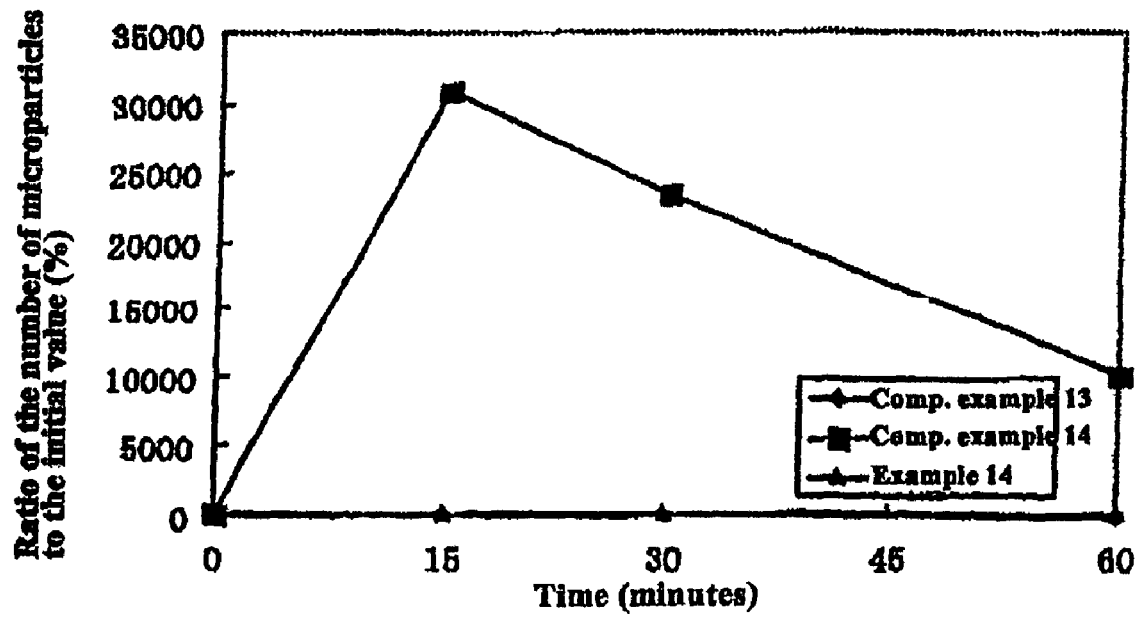
FIG. 7 is a diagram showing changes over time in the number of insoluble particulate matter determined in Comparative Example 13, Comparative Example 14, and Example 14.

Five milliliters aqueous 0.5 mg/ml compound B solution were prepared and 5 ml aqueous 30 mg/ml E-SD solution and 0.1 ml aqueous 15.12 mg/ml sodium bicarbonate solution were added to this and thoroughly mixed to obtain a prepared liquid. Two milliliters aqueous 10 mg/ml magnesium chloride.6H$_2$O were added to this prepared liquid, and the number of insoluble particulate matter (2 µm or larger) was determined 0, 15, 30 and 60 minutes after addition by the same method as in Experiment 11. The changes over time in the number of insoluble particulate matter determined in above-mentioned Comparative Example 13, Comparative Example 14, and Example 14 are shown in FIG. 7.

<Results and Discussion>

According to the results in Comparative Example 13 and Comparative Example 14, there was an increase in the number of insoluble particulate matter when aqueous magnesium chloride solution was added to aqueous compound B solution. The formation of insoluble particulate matter was inhibited when aqueous magnesium chloride solution was added to aqueous compound B solution in which E-SD had been dissolved in Example 14. This confirms that aminoalkyl methacrylate copolymer E has the effect of inhibiting the formation of slightly soluble complex between compound B and metal (magnesium) ions.

EXAMPLE 15

Amount of Acid and Type of Acid Added to Eudragit E

First, 1,500 g Eudragit™ E100 and 150 g Tween 80 were dissolved in a mixture of 9,000 g ethanol and 3,000 g 1 mol/l hydrochloric acid to make the spraying liquid. The spraying liquid was spray dried under conditions of a spraying speed of 30 g/min, an intake temperature of 85° C., and an exhaust temperature of 62-66° C. using the model L-8 spray dryer (Ohkawara Seisakujo) and dried for 24 hours at 40° C. to obtain a white powder. When 1 g of this product was added to 15 ml purified water, it completely dissolved. Moreover, this product was stable with no aggregation during storage.

EXAMPLE 16

First, 2.9 g Eudragit™ EPO, which is a micropowder of Eudragit™ E, were added to 50 g purified water to make the test liquid. When 650 mg citric acid were added to this test liquid, the Eudragit™ E in the test liquid completely dissolved. A white lyophilized product was obtained when a solution of 0.25 g Tween 80 dissolved in this liquid was lyophilized using the model FD-81 lyophilization device (Tokyo Rika Kikai Co., Ltd.). When 1 g of this product was added to 15 g purified water, it completely dissolved.

EXAMPLE 17

First, 2.9 g Eudragit™ EPO were added to 50 g purified water to make the test liquid. When 650 mg tartaric acid were added to this test liquid, the Eudragit™ E in the test liquid completely dissolved. A white lyophilized product was obtained when a solution of 0.29 g Tween 80 dissolved in this liquid was lyophilized as in Example 16. When 1 g of this product was added to 15 g purified water, it completely dissolved.

EXAMPLE 18

3.3 g Eudragit™ EPO were added to 50 g purified water to make the test liquid. When 650 mg D,L-malic acid were added to this test liquid, the Eudragit™ E in the test liquid completely dissolved. A white lyophilized product was obtained when a solution of 0.33 g Tween 80 dissolved in this liquid was lyophilized as in Example 16. When 1 g of this product was added to 15 g purified water, it completely dissolved.

<Results and Discussion>

The results of Example 15 indicates that it is possible to prepare aminoalkyl methacrylate copolymer E to which an acid that can dissolve in purified water has been added by adding 0.075 parts by weight of hydrochloric acid to 1 part by weight of Eudragit™ E. Consequently, this composition apparently will dissolve in the stomach as well as in the entire digestive tract where water can be present to improve drug absorption in the digestive tract. The results of Examples 16~18 show that it is possible to prepare aminoalkyl methacrylate copolymer E that will dissolve in purified water, regardless of the type of acid, such as citric acid, tartaric acid, malic acid, etc.

EXPERIMENT 12

(Control 5)<Type of Acid: Confirmation of Performance In Vivo>

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. A PBS solution of 0.4 mg/ml compound B was administered through this loop so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained.

EXAMPLE 19

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Administration liquid of the spray-dried product in Example 15 dissolved in a PBS solution of 0.4 mg/ml compound B to a concentration of 0.5 mg/ml was administered so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained.

EXAMPLE 20

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Administration liquid of the lyophilized product in Example 16 dissolved in a PBS solution of 0.4 mg/ml compound B to a concentration of 0.5 mg/ml was administered so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained.

EXAMPLE 21

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Administration liquid of the lyophilized product in Example 17 dissolved in a PBS solution of 0.4 mg/ml compound B to a concentration of 0.5 mg/ml was administered so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained.

EXAMPLE 22

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Administration liquid of the lyophilized product in Example 18 dissolved in a PBS solution of 0.4 mg/ml compound B to a concentration of 0.5 mg/ml was administered so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained.

EXAMPLE 23

Laparotomy was performed under pentobarbital (brand name Nembutal, Dainabot Co., Ltd.) anesthetization in Wistar male rats (8 weeks old) and the Treitz's ligament and ileocecal juncture were bound with thread to form an intestinal loop. Next, 111 mg of a solution prepared by dissolving 400 mg Eudragit™ EPO and 40 mg Tween 80 in 4 g linoleic acid were measured out and added to 20 mL of a PBS solution of 0.4 mg/ml compound B to prepare the administration liquid. This administration liquid was administered through the loop so that the dose would be 10 mg/kg compound B. Blood was drawn from the jugular vein 0, 0.25, 0.5 and 1 hour after administration and the plasma concentration of unaltered form (ng/ml) was determined by the same method as in Control 4. The area under concentration curve (AUC) was calculated from the changes in the plasma concentration that were obtained. The AUC found in Control 5 and Examples 19~23 are shown in Table 7.

TABLE 7

| | AUC (ng · h/ml) |
|---|---|
| Control 5 | 42.2 ± 11.3 |
| Example 19 | 393.6 ± 135.7 |
| Example 20 | 1367.8 ± 1054.5 |
| Example 21 | 339.1 ± 162.0 |
| Example 22 | 635.6 ± 381.2 |
| Example 23 | 504.0 ± 698.0 |

(Mean value ± S.D., n = 3)

<Results and Discussion>

The AUC in any of Examples 19~23 was high in comparison to Control 5.

The AUC was high in comparison to Control 5 whether hydrochloric acid, citric acid, tartaric acid, malic acid, linoleic acid, etc., was used as the type of acidic substance uniformly mixed in Eudragit E. Consequently, it was clear that the acidic substance uniformly mixed with aminoalkyl methacrylate copolymer E has the effect of promoting absorption of compound B from the digestive tract, regardless of the type of acid.

EXPERIMENT 13

Control 6

Ten milligrams compound B and 190 mg lactose were mixed and control tablets were prepared by tableting under a tableting pressure of 40 kg/cm$^2$ using an oil press. Fifty grams of feed (Science Diet®, Nippon Hill's) were given to beagles (15-24 months old) that had been fasted over night and 30 minutes later, the control tablets were orally administered together with 30 ml water. Approximately 3 ml blood were drawn from the brachial veins of the front limbs over time up to 14 h after administration and the plasma concentration of unaltered form (ng/ml) was determined by the same method as Comparative Example 6. The maximum plasma concentration (Cmax) and area under concentration curve (AUC) were calculated from the changes in the plasma concentration that were obtained.

EXAMPLE 24

Ten milligrams compound B, 125 mg E-SD, and 65 mg sucrose were mixed and tablets were prepared by tableting under a tableting pressure of 40 kg/cm$^2$ using an oil press to obtain a core. Two-hundred milligrams polyethylene oxide (Polyox WSR303, Union Carbide Co., Ltd.) and 100 mg Macrogol 6000 were mixed to prepare polyethylene oxide/Macrogol 6000 mixed powder. Half was added to a mortar for tableting and then the core was placed in the center of the mortar. Next, half of the remainder of the above-mentioned mixed powder was added to the mortar and tablets with an outer layer were prepared by tableting under a tableting pressure of 40 kg/cm$^2$ using an oil press. This dry-coated tablet was orally administered to beagles under the same conditions as in Experiment 13, blood was drawn over time up to 14 h after administration, and the plasma concentration of unaltered form was determined. Cmax and AUC were calculated from the changes in the plasma concentration that were obtained. The results of Experiment 13 and Example 24 are shown in Table 8.

TABLE 8

|  | Cmax (ng/ml) | AUC (ng · h/ml) |
| --- | --- | --- |
| Test 13 | 1.0 ± 1.0 | 4.7 ± 3.9 |
| Example 24 | 12.3 ± 5.4 | 55.8 ± 26.4 |

(Mean value ± S.D., n = 3-6)

<Results and Discussion>

Compound B is a drug that is readily affected by food and, as shown by the results of Experiment 13, it has a low Cmax and AUC when taken with food. In contrast to this, the Cmax and AUC of Example 24 increased to approximately 12-times those of experiment 13. This results indicate that a reduction in absorption of a drug due to the effects of food can be prevented by using a timed-release pharmaceutical preparation with which aminoalkyl methacrylate copolymer E and an acidic substance, such as hydrochloric acid, etc., has been uniformly mixed.

Possibility of Industrial Application

Aminoalkyl methacrylate copolymer E, which is used as the effective component in the present invention, has the effect of enhancing drug permeability in the digestive tract mucous membrane and/or mucous layer and therefore is useful as an excellent agent for improving oral absorption. The pharmaceutical composition of the present invention can enhance drug permeability by the effect of inhibiting a reduction in drug permeability of the mucous layer based on interaction between the components of the digestive tract mucous membrane and/or mucous layer and drug and thereby realize excellent oral absorptivity of drugs whose oral absorption has been considered to be reduced in the past. Moreover, in addition to drugs that are difficult to absorb, the pharmaceutical composition of the present invention is ideal for drugs that show normal absorptivity and therefore, it can be widely used.

What is claimed is:

1. A method of improving oral absorption in the digestive tract of an oral drug by orally administering a pharmaceutical composition obtained by bringing the drug which is difficult to absorb, which forms an insoluble complex, an aminoalkyl methacrylate copolymer E, an acidic substance together and uniformly mixing at least the polymer and said acidic substance, wherein said pharmaceutical composition is 1 or 2 or more selected from the group consisting of granules, tablets, capsules, and liquid; and wherein the $C_{max}$ and AUC of said drug is increased in the presence of said copolymer E and said acidic substance, and wherein the ratio of said polymer is 0.5~250 parts by weight per 1 part by weight of the drug and the acidic substance is used in the amount that will neutralize 10% or more of the basic groups of aminoalkyl methacrylate copolymer E and wherein the digestive tract is the small intestine consisting of the duodenum, jejunum, and ileum, and the large intestine consisting of the colon, the ascending colon, transverse colon, descending colon, and sigmoid colon, and the rectum, wherein said pharmaceutical composition has improved absorption in the digestive tract.

2. The method of claim 1, wherein a pharmaceutical composition obtained by uniformly mixing said drug, said aminoalkyl methacrylate copolymer E, and said acidic substance is used.

3. The method of claim 1, wherein the aminoalkyl methacrylate copolymer E is used in an amount of 0.5 parts by weight or more per 1 part by weight drug.

4. The method of claim 1 wherein the acidic substance that is used is one with which when 1 g of said substance is dissolved in 50 ml water, pH of said solution is brought to 6 or lower.

5. The method of claim 1, wherein pharmaceutical composition is used which comprises 0.5~50 parts by weight aminoalkyl methacrylate copolymer E in terms of 1 part by weight drug in the amount effective to treat disease, and said acidic substance is present in an amount that will neutralize 10% or more of basic groups of the polymer.

6. The method of claim 1, wherein a pharmaceutical composition is used which comprises 0.5~50 parts by weight aminoalkyl methacrylate copolymer E per 1 part by weight drug in an amount effective for treatment of disease, and 0.005~50 parts by weight acidic substance per 1 part by weight of the polymer.

7. The method of claim 1, wherein a composition is used where the aminoalkyl methacrylate copolymer E and acidic substance are granulated.

8. The method of claim 1, wherein the aminoalkyl methacrylate copolymer E and acidic substance are dissolved in a pharmaceutically acceptable solvent and/or used as a spray-dried substance that has been obtained by spray drying said solution or used as a lyophilized substance that has been obtained by lyophilization of said solution.

9. The method of claim 1, wherein the aminoalkyl methacrylate copolymer E and acidic substance is used in a state of dissolution and/or suspension in a pharmaceutically acceptable solvent.

10. The method of claim 1, wherein the drug is a member of the group consisting of a compound, a compound salt, a liquid, a suspension, an emulsion and a crystal polymorph.

11. The method of claim 1, comprising a layer in which the aminoalkyl methacrylate copolymer E and acidic substance have been uniformly mixed and coated on a core of said drug.

12. The method of claim 1, wherein the $C_{max}$ and AUC of said drug is increased in the presence of said copolymer E and said acidic substance approximately 4-times and 7-times, respectively.

13. The method of claim 1, wherein the $C_{max}$ and AUC of said drug is increased in the presence of said copolymer E and said acidic substance approximately 4.5-times and 8-times, respectively.

14. The method of claim 1, wherein the $C_{max}$ and AUC of said drug is increased in the presence of said copolymer E and said acidic substance approximately 3-times and 6-times, respectively.

15. The method of claim 1, wherein the $C_{max}$ and AUC of said drug is increased in the presence of said copolymer E and said acidic substance approximately 7.4-times and 5.7-times, respectively.

16. The method of claim 1, wherein the $C_{max}$ and AUC of said drug is increased in the presence of said copolymer E and said acidic substance approximately 4-times and 7-times, respectively.

17. The method of claim 1, wherein each of the $C_{max}$ and AUC of said drug is increased in the presence of said copolymer E and said acidic substance approximately 12-times.

* * * * *